United States Patent [19]
Yamaguchi et al.

[11] Patent Number: 5,912,721
[45] Date of Patent: Jun. 15, 1999

[54] GAZE DETECTION APPARATUS AND ITS METHOD AS WELL AS INFORMATION DISPLAY APPARATUS

[75] Inventors: Osamu Yamaguchi; Yasukazu Okamoto; Kazuhiro Fukui, all of Tokyo, Japan

[73] Assignee: Kabushiki Kaisha Toshiba, Kawasaki, Japan

[21] Appl. No.: 08/816,453

[22] Filed: Mar. 12, 1997

[30] Foreign Application Priority Data

Mar. 13, 1996 [JP] Japan .................................. 8-056503
Mar. 15, 1996 [JP] Japan .................................. 8-059071

[51] Int. Cl.[6] .............................. A61B 3/14; A61B 3/00
[52] U.S. Cl. .......................... 351/210; 351/209; 351/246
[58] Field of Search ..................................... 351/210, 209, 351/206, 205, 200, 211, 221, 246, 247

[56] References Cited

U.S. PATENT DOCUMENTS 4,973,149 11/1990 Hutchinson .............................. 351/210

FOREIGN PATENT DOCUMENTS 2-134130 5/1990 Japan .
4-372012 12/1992 Japan .

Primary Examiner—Hung Xuan Dang
Attorney, Agent, or Firm—Finnegan, Henderson, Farabow, Garrett & Dunner, L.L.P.

[57] ABSTRACT

Apparatus disclosed herein includes an information presentation section 120 for performing presentation of information selected, a gaze-point detecting section 130 for estimating the user's gaze point, a display change section 150 for changing the display method of a display portion of information being selected by the user, a prediction section 140 for predicting information to be selected by the user, an intention transmission section 160 for transmitting to the system determination of information which the user wants to input, and a result output section 170 for storing therein the selected information and for sending forth it to another device or apparatus, thereby enabling easy and rapid selection of information by use of the user's gaze-point information.

18 Claims, 36 Drawing Sheets

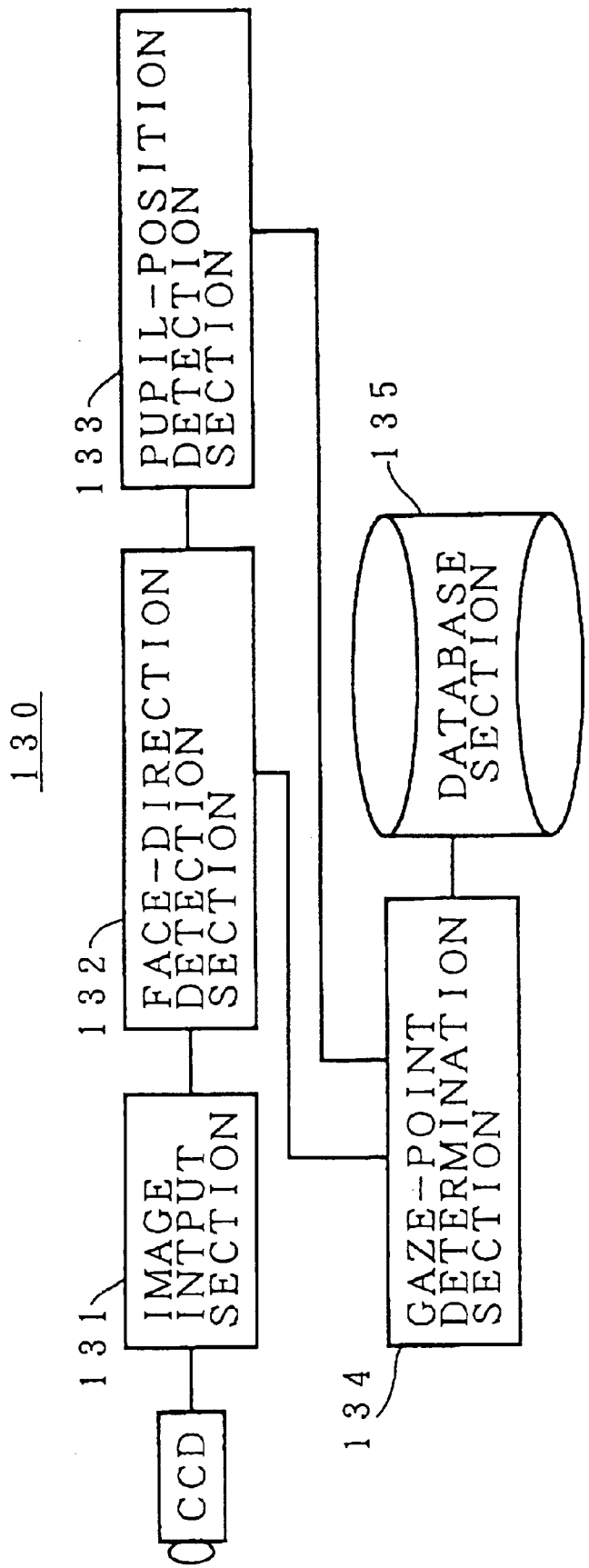

FIG.23A
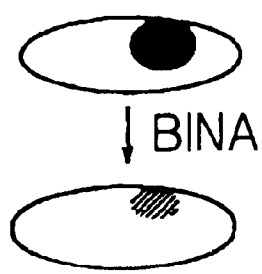
FIG.23B
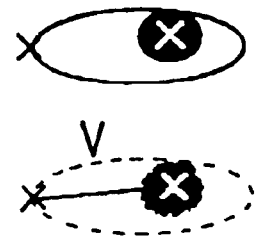 
FIG.23C
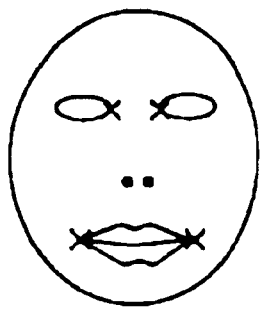 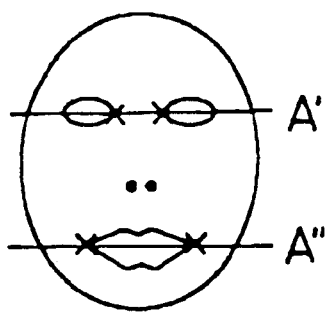

FIG.26B1
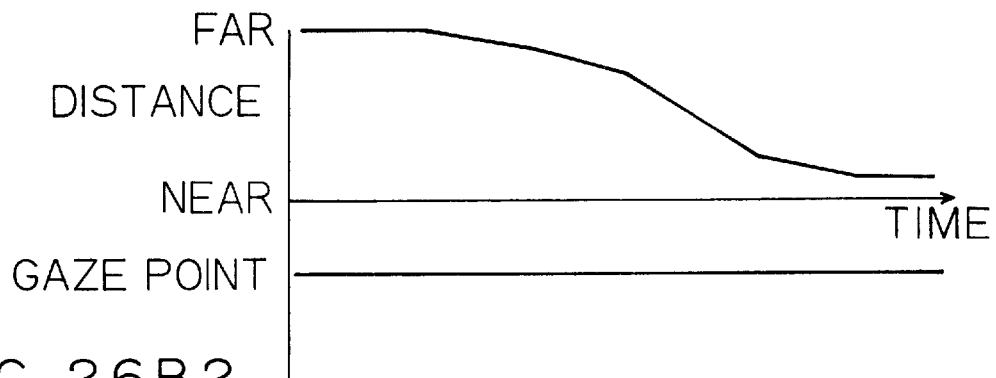
FIG.26B2
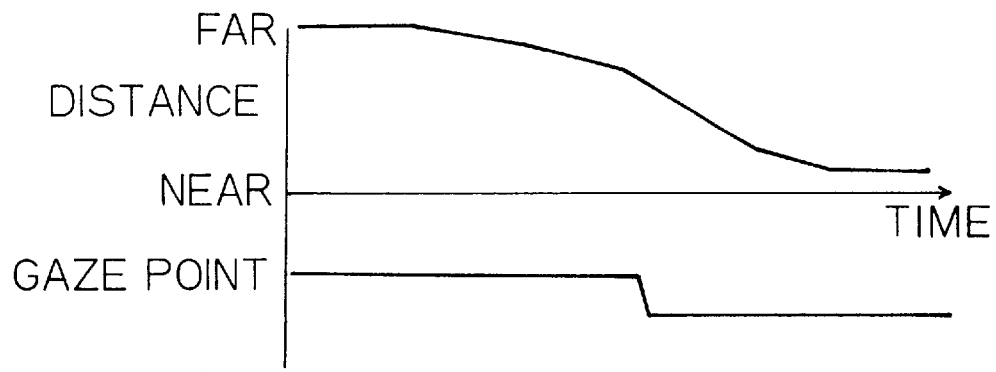
FIG.26B3
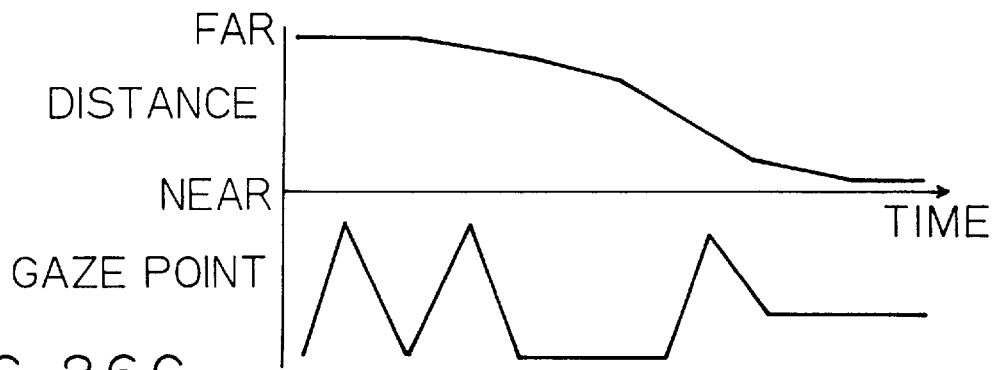
FIG.26C
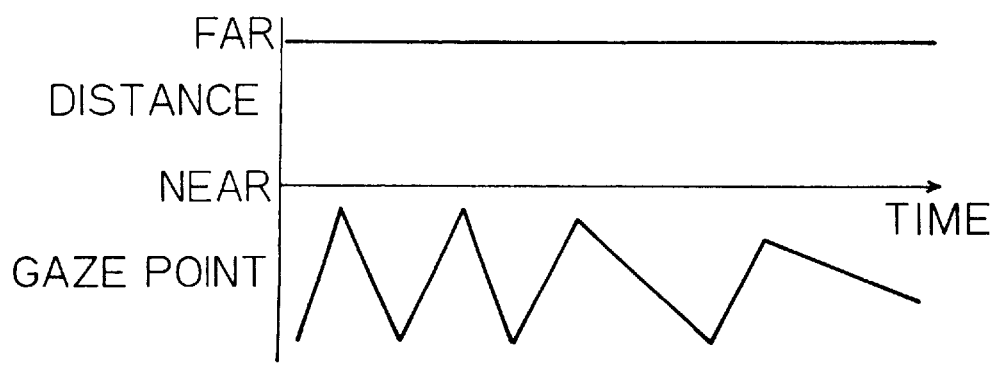

FIG.27
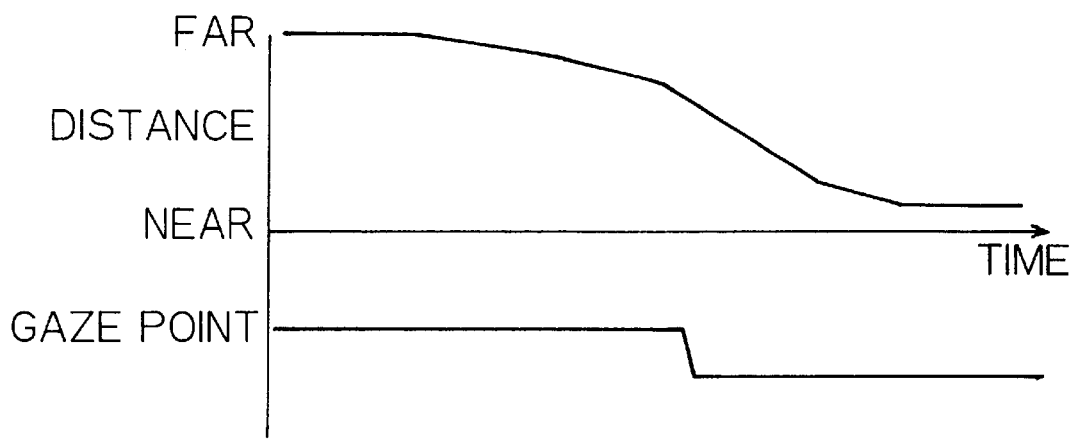
| 0:02 | 0:03 | 0:04 | 0:05 | 0:06 | 0:07 | 0:08 | 0:09 |
|---|---|---|---|---|---|---|---|
| (x1,y1) | (x1,y1) | (x1,y1) | (x1,y1) | (x2,y2) | (x2,y2) | (x2,y2) | (x2,y2) |
| 5.0 | 5.0 | 4.0 | 4.0 | 3.0 | 2.0 | 1.0 | 0.6 |
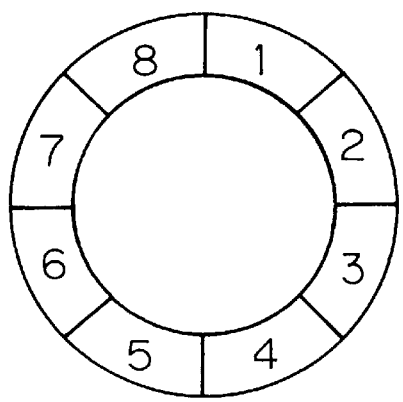

: GAZE-POINT POSITION

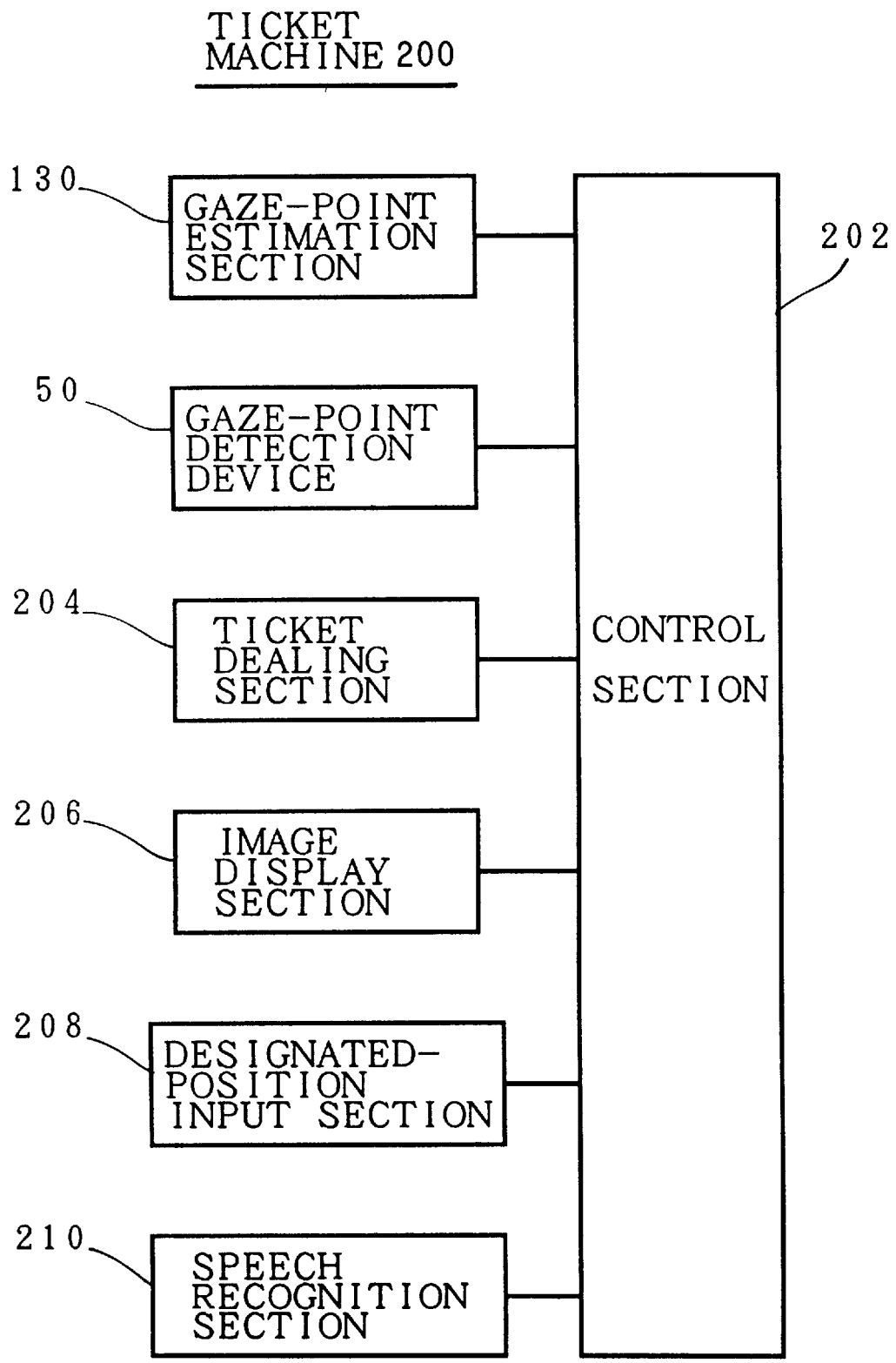

GAZE DETECTION APPARATUS AND ITS METHOD AS WELL AS INFORMATION DISPLAY APPARATUS

TECHNICAL FIELD

The present invention relates to gaze detection apparatus for detecting certain position as designated by the line of sight—namely, the user's gaze point—and the method thereof.

PRIOR ART

Where computer users do their required works while viewing the display screen of a computer system, tasks of designating a specific position on the screen will possibly occur, such as selection of one from several windows being displayed in multiwindow systems, for example. In the presently available computer systems, the user's operations for designation of a desired screen position are attained by manually operating an associated mouse device.

Concerning this, in a gaze-point movement analysis apparatus disclosed in Published Unexamined Japanese Patent Application (JPA) No. 4-49943 (04049943), there is proposed a device for allowing the user to designate a position on the screen by detecting the user's gaze point thereon.

This device comes with a sensor for detecting the user's gaze point and a sensor for detecting the attitude of user's head; the device is responsive to the outputs of the both sensors for computing the direction of user's gaze point in the 3D space. Due to such arrangement, the prior art is faced with a problem that the necessity of attaching two separate sensors to the user's head serves to impose a burden on the user. Another problem is that high accuracy is not expectable due to accumulation of errors of two sensors in the direction of gaze point calculated. This is because of the fact that the gaze direction is calculated by addition of detection results of the two sensor outputs which are for detection of the head attitude and gaze point directions with respect to the user's head.

One prior known approach to avoid the problems is disclosed in "Non-Intrusive Gaze Tracking Using Artificial Neural Network", Shumeet Baluja, Dean Pomerleau, Advances in Neural Information Processing systems 6 Cowan J. D, Tesauro, G. & Alspector, J.(eds) Morgan Kaufman Publishers, 1994, wherein apparatus is proposed which estimates the gaze direction by inputting to the neural network an image representing a photograph of a selected area near or around the eyes in images. However, this apparatus suffers from a problem that it can be influenced with variations in the illumination condition of operation environment and a change in the user's head position due to the fact that the apparatus disclosed therein is arranged to make use of the entire regions of the "near-the-eye" region image photographed. Another problem is that since the gaze direction estimation is based on person-to-person variable information, such as the near-the-eye region image, it should be required that the neural network must "learn" in advance by use of a great number of different images.

A further problem with the prior art method is that since the user's gaze direction relative to a camera is calculated, the position of the camera relative to an object to be indicated by the user's gaze point is fixed and cannot be moved during operations. In order to detect the gaze point while permitting movement of the user's head with the camera fixed at a location, it is required that the camera offer extended gaze-point range; however, this does not come without accompanying a penalty that the resolution per pixel decreases with an increase in view field causing the gaze detection accuracy to decrease accordingly.

As has been described above, the prior art technique for detecting the gaze point of the user have problems. The technique of attaching sensors to the user disadvantageously serves to create the user's burden. On the other hand, with the gaze detection scheme of detecting the gaze point using images as photographed by cameras, the gaze point measurement remains less in accuracy because person-to-person variable information is detected for use in estimating the gaze direction while forcing the direction of camera to be fixed or stationary leading to a decrease in resolution.

The present invention has been made in view of the foregoing problems, and an object of the invention is to provide a gaze detection apparatus and its method capable of easily and accurately detecting the position as indicated by the user's gaze point on a display device such as a computer display.

Additionally, in interactive apparatus or systems such as vending machines, ticket selling machines and the like, or in information presentation apparatus such as OA equipment including personal computers and workstations, or tourist information guidance equipment, on occasions where consumers' desired products, tickets or information is to be transferred to the system, there is known an input method for selection of one or several presently displayed items by means of buttons, keyboards, mouse devices or by use of a touch-panel on the screen.

However, it can happen that users are incapable of rapidly performing manual operations, or required instructions can sufficiently be carried out without having to use their hands. If this is the case, when the consumers' intention is input, the aforesaid input devices will disturb the human's activity while compelling time-consuming and troublesome operations.

Especially, in view of the fact that recent advanced devices come with an increased number of buttons, where consumers select their desired information or product item, they are required to follow a series of actions such as "recognizing the entire system arrangement→searching for a desired one while viewing the display screen→carrying a hand to a corresponding location." This means that much time is required for them to finally select one preferred item. Accordingly, it has been considered that a different input means is needed for certain systems that are strictly required to achieve rapid responses.

Gaze detection is developed as a method for performing position selection without having to use hands. Information items obtainable by a gaze point may include not only positional information but also human's intention, expression of will and others enabling easy attainment of works of selecting any interesting part or item from among a plurality of objects being presently indicated.

Conventionally, a number of inventions have been made for detection of a gaze point, which may be grouped into two main categories which follow.

First, the contact type ones employing a glasses-like tool such as an eye camera; second, non-contact type ones which detect a human's gaze point from an image as photographed by use of a CCD camera or the like.

The contact type apparatus is arranged to attach a tool such as glasses, goggles or the like, which tool has a detector device attached thereto for input of a gaze point.

The non-contact type apparatus is designed to employ a CCD camera image-capturing the face of a target person at a distant location, detecting the direction of gaze point by using the feature of a near-the-eye region(s).

For example, JPA 04255015 discloses therein a technique of obtaining relative movement amount of a gaze point from a change in the center coordinates of an extracted pupil in the pupil's contour data. This invention suffers from accumulation of errors: While this invention also has a mechanism for compensating for such error accumulation, it remains insufficient.

Another approach is disclosed in JPA 03017696, wherein for the purpose of using a gaze point to control the position of a cursor of word-processors or the like, an eye region is divided into subregions by a vertical and a horizontal line passing through the center of pupil in an eye region, then calculating the position of such gaze point with the area ratio of divided subregions being as the characteristic amount.

Generally, a problem faced with the gaze detection is that increasing the accuracy of gaze detection requires either the contact type or user's physical constraints, such as fixing the head. Another problem is that it is difficult to employ as an input device any arrangements which may disturb human's natural actions or those requiring or compelling troublesome attachment of certain tool to the user's body.

An input device using a gaze point is disclosed in JPA 04372012, which employs in combination speech recognition, gaze detection, and action detection such as eye's blinking actions for attaining input of information by complementarily using them to effect transmission of intentions.

Also, in some publications ("Integrating Simultaneous Input from Speech, Gaze, and hand Gestures", David B. Noons, Carlton J. Sparrell, and Kristinn R. Thorisson; "Intelligent Multimedia Interfaces," Edited by Mark T. Maybury, MIT Press (1993)), there is disclosed a synthesis method for an interface using gaze point, speech recognition, and hand gestures. This proposed system is designed to attain bidirectional or interactive transmission of map information and perform operations in the 3D block world.

Most of the above inventions using the gaze point may be adapted for use mainly as an alternative of the currently available keyboard units or mouse devices; here, the problem as to the accuracy of gaze detection still remains.

Incidentally, an input device using the gaze point is disclosed in JPA 04372012. In the input device disclosed, presentation of information is exclusively limited to display applications; and, its primary object is to identify by the gaze point one from several icons or equivalents thereof as visually indicated on the display screen and to operate using an audible instruction means. However, in order to attain such operations, high-accuracy gaze detection means should be required. To attain an alternative of the interface such as currently available mouse devices, several difficulties are found.

In view of the foregoing problems, an object of-the present invention is to provide a scheme capable, by taking account of the accuracy of gaze-point detection, of successfully presenting information as selected by users and easily selecting information without having to require needlessly high accuracy for gaze detection. For example, selecting information can be attained by efficiently presenting information even in the case of preparing a gaze-point detection means capable of recognizing the degree of four-divided portions of a display.

Further, simultaneous use of the gaze point and other operations enables achievement of "search for a desired item of information→selection" thus making it possible to provide an interface which allows users to act naturally. It is also an object of the invention to enable determination of a gaze point and rapid selection of information as well as designation thereof by using a gaze-direction detection result at a time point whereat intention transmission was done, by for example allowing users to select any preferred product, information and location based on their gaze point, then depressing one button implemented or audibly generating or vocalizing a corresponding phrase that has been set or registered in advance.

Furthermore, in the case of pre-assuming human's activity while allowing the system to present information, it is possible to lighten the user's workload on selection of information by presenting information that is considered to be the most optimal one. Also, it is a further object of the invention to provide easy-to-use apparatus for operators by controlling, upon input, the so-called "timing" that dynamically changes which information item is to be selected at which time point.

SUMMARY OF THE INVENTION

The invention as recited in claim 1 is a gaze detection apparatus characterized by comprising image input means for sensing an image of the user, eye detection means for detecting the eyes of said user from said image as sensed by said image input means, pupil detection means for obtaining the position of pupils in said eyes detected by said eye detection means, three or more light emission means for emitting light toward said user, reference-point detection means for detecting respective reflecting positions of illumination light of said three or more light emission means on the eyes of said user, and gaze-point detection means for detecting the gaze point of said user based on the three or more reflecting positions detected by said reference-point detection means and the positions of said pupils detected by said pupil detection means.

The gaze detection apparatus recited in claim 1 operates to sense or photograph the imaging of light emitted from the light emission means on the eye balls, and calculate or compute the direction of such gaze point by comparing the pupil's position in the photographed image with the reflecting positions of the light emission means.

The invention as recited in claim 2 is a gaze detection apparatus according to claim 1, characterized in that said eye detection means compares said image sensed by said image input means with the three or more reflecting positions detected by said reference-point detection means thereby determining as eyes the near-field or nearby region of said reflecting positions in said image.

The gaze detection apparatus as recited in claim 2 is capable of accurately and reliably identifying the user's gazing position due to the fact that said eye detection means determines the nearby region of said reflecting position in said image by comparing said image photographed by said image input means with the three or more reflecting positions detected by said reference-point detection means.

The invention of claim 3 is a gaze detection apparatus according to claim 1, characterized in that said gaze-point detection means detects three or more reflecting positions to be detected by said reference-point detection means and said pupil positions to be detected by said pupil detection means with the light emission position of each said three or more light emission means as a reference.

In the gaze detection apparatus as recited in claim 3, the image input means such as a camera may be placed at any desired locations insofar as said three or more light emission means are definite in position because of the fact that said instruction-position detection means obtains said three or more reflecting positions of said reference-point detection means and said pupil's positions of said pupil-position detection means with the light emission position of each said three or more light emission means being as a reference.

The invention of claim 4 is a gaze detection method characterized by comprising an image input step for sensing an image of the user, an eye detection step for detecting eyes of said user from said image sensed by said image input means, a pupil detection step for obtaining the position of pupils in said eyes detected at said eye detection step, a reference-point detection step for detecting on the eyes ofsaid user respective reflecting positions of illumination light of three or more light emission means for emitting light toward said user, and a gaze-point detection step for detecting the gaze point of said user based on the three or more reflecting positions detected at said reference-point detection step and the positions of said pupils detected at said pupil detection step.

The invention of claim 5 is a gaze detection method according to claim 1, characterized in that said eye detection step compares said image sensed at said image input step with the three or more reflecting positions detected at said reference-point detection step thereby determining as eyes the near-field region of said reflecting positions in said image.

The invention of claim 6 is a gaze detection method according to claim 4, characterized in that said gaze-point detection step detects three or more reflecting positions to be detected at said reference-point detection step and said pupil positions being detected at said pupil detection step with the light emission position of each said three or more light emission means being as a reference.

The invention of claim 7 is a gaze detection apparatus characterized by comprising image input means for inputting an-image of the user, face image extraction means for extracting a face image of said user from said image as input by said image input means, eye's inner corner detection means for detecting the position of an inner corner of at least one eye from said face image extracted by said face extraction means, pupil detection means for detecting the position of a pupil in said eye from the face image extracted by said face extraction means, and gaze-point detection means for obtaining a vector extending from the position of said inner corner of the eye detected by said inner corner of the eye detection means to the position of said pupil detected by said pupil detection means and for making use of the obtained vector to detect a gaze point of said user.

The invention of claim 8 is a gaze detection apparatus characterized by comprising image input means for inputting an image of the user, face image extraction means for extracting a face image of said user from said image as input by said image input means, eye detection means for detecting the position of an inner corner of the eye (tear duct part) or an outer corner of the eye of at least one eye from said face image extracted by said face extraction means, mouth/nose detection means for detecting the position of a mouth or a nostril(s) from the face image extracted by said face extraction means, face direction calculation means for calculating a face direction plane connecting between the inner corner of the eye positions or outer corner of the eye positions of the both eyes detected by said eye detection means and the position of the mouth or nostrils detected by said mouth/nose detection means, and gaze-point detection means for detecting a gaze point of said user based on a perpendicular vector of said face direction plane calculated by said face direction plane calculation means.

The invention of claim 9 is an information display apparatus for allowing the user to select one from a plurality of information items, characterized by comprising gaze-point detection means for detecting a gaze point of the user of said information display apparatus, prediction means for predicting information as required by said user based on said gaze point detected by said gaze-point detection means, and information display means for performing displaying of the information predicted by said prediction means.

Whereby, the user makes a selection by the gaze point, wherein the gaze-point direction is used by the gaze-point detection means to detect the gaze point while the prediction means predicts an item to be selected, such as desired information, commercial products or the like, which will then be displayed by the information display means. Accordingly, it is possible to lighten the user's workload upon selection.

The invention of claim 10 is an information display apparatus according to claim 9, characterized in that said prediction means comprises prediction change means for, when said gaze point detected by said gaze-point detection means is moved, predicting again or "repredicting" information as necessary for said user on the basis of said gaze point moved, and display change means for instructing said information display means so as to display the information repredicted by said prediction change means.

Employing such an arrangement enables the user by himself using the gaze point to become aware of which one of information items is presently selected while allowing the display change means to change or modify certain information display portion existing at the gaze point in order to attain suitable display as predicted.

The invention of claim 11 is an information display apparatus according to claim 9, characterized in that where said gaze point detected by said gaze-point detection means is within said information display means, said prediction means predicts information necessary for said user on the basis of such steadily looked information, and that where said gaze point detected by said gaze-point detection means is out of said information display means, said prediction means predicts information necessary for said user based on that steadily looked portion.

It is thus possible to change or modify the display contents depending upon the activity of gazing at locations other than the information display means.

The invention of claim 12 is a gaze detection method for detecting a gaze point of the user, characterized by comprising an image input step for inputting an image of said user, a face image extraction step for extracting a face image of said user from said image as input at said image input step, an inner corner of the eye detection step for detecting the position of a inner corner of the eye or "inner corner of the eye" of at least one eye from said face image extracted at said face extraction step, a pupil detection step for detecting the position of a pupil in said eye from the face image extracted at said face extraction step, and a gaze-point detection step for obtaining a vector that extends from the position of said inner corner of the eye detected at said inner corner of the eye detection step to the position of said pupil detected at said pupil detection step and for using the obtained vector to detect a gaze point of said user.

The invention of claim 13 is a gaze detection method for detecting a gaze point of the user, characterized by comprising an image input step for inputting an image of said user, a face image extraction step for extracting a face image of said user from said image as input at said image input step, an eye detection step for detecting the position of an inner corner of the eye (tear duct part) or an outer corner of the eye of at least one eye from said face image extracted at said face extraction step, a mouth/nose detection step for detecting the position of a mouth or a nostril(s) from the face image extracted at said face extraction step, a face direction calculation step for calculating a face direction plane connecting between the inner corner of the eye positions or outer corner of the eye positions of the both eyes detected at said eye detection step and the position of the mouth or nostrils detected at said mouth/nose detection step, and a gaze-point detection step for detecting a gaze point of said user based on a perpendicular vector of said face direction plane calculated at said face direction plane calculation step.

The invention of claim 14 is an information display method for allowing the user to select one from a plurality of information items, characterized by comprising a gaze-point detection step for detecting a gaze point of the user of said information display apparatus, a prediction step for predicting information as required by said user on the basis of said gaze point detected at said gaze-point detection step, and an information display step for performing displaying of the information as predicted at said prediction step.

The invention of claim 15 is an information display method according to claim 14, characterized in that said prediction step comprises a prediction change step for, when said gaze point detected at said gaze-point detection step is moved, repredicting information necessary for said user on the basis of said gaze point moved, and a display change step for instructing said information display means so as to display the information repredicted at said prediction change step.

The invention of claim 16 is an information display method according to claim 14, characterized in that where said gaze point detected at said gaze-point detection step is within said information display means, said prediction step estimates information necessary for said user based on the steadily looked information thereof, and that where said gaze point detected at said gaze-point detection step is out of said information display means, said prediction step predicts information necessary for said user on the basis of that steadily looked portion.

The invention of claim 17 is an information display apparatus for displaying information, characterized by comprising distance measurement means for obtaining the distance between said information display apparatus and the user thereof, gaze-point detection means for detecting a gaze point of said user by selecting a detection method of gaze point in accordance with the distance measured by said distance measurement means, prediction means for predicting information required by said user on the basis of said gaze point detected by said gaze-point detection means, and information display means for performing displaying of the information predicted by said prediction means.

Whereby, judgment will be more reliable due to the fact that where the user by himself judges which information item is presently selected by the gaze point, the gaze-point detection means selects an appropriate gaze detection method in accordance with resultant distance as measured by the distance measurement means and then detects said user's gaze point.

The invention of claim 18 is an information display method for displaying information by use of information display means, said method comprising a distance measurement step for obtaining the distance between said information display means and the user thereof, a gaze-point detection step for detecting a gaze point of said user by selecting a detection method of gaze point in accordance with the distance measured at said distance measurement step, a prediction step for predicting information required by said user on the basis of said gaze point detected at said gaze-point detection step, and an information display step for performing displaying of the information as predicted at said estimation step.

BRIEF DESCRIPTION OF THE DRAWINGS

FIG. 20 is a block diagram of a gaze-point detecting section 130.

FIGS. 23A–23C are diagrams for explanation of a pupil position detecting section 133.

FIGS. 26B1–26B3 and 26C are diagrams showing several examples of the activity pattern.

FIG. 27 is a diagram showing examples of information storage in an information recording section 143.

FIG. 40 is a block diagram of a ticket selling machine 200 in accordance with a sixth embodiment.

EMBODIMENTS OF THE INVENTION

First Embodiment

A first embodiment relating to this invention will be explained with reference to the accompanying drawings.

It should be noted that the term "gaze point" as used herein refers to a point or part being pointed out and instructed by human's line of sight or "view line" as applied thereto. Note also that in the description, this term "gaze point" is used to mean not only the exact pin point whereat the view line is applied but also near-field region having certain wideness in the vicinity thereof.

Figure 1:
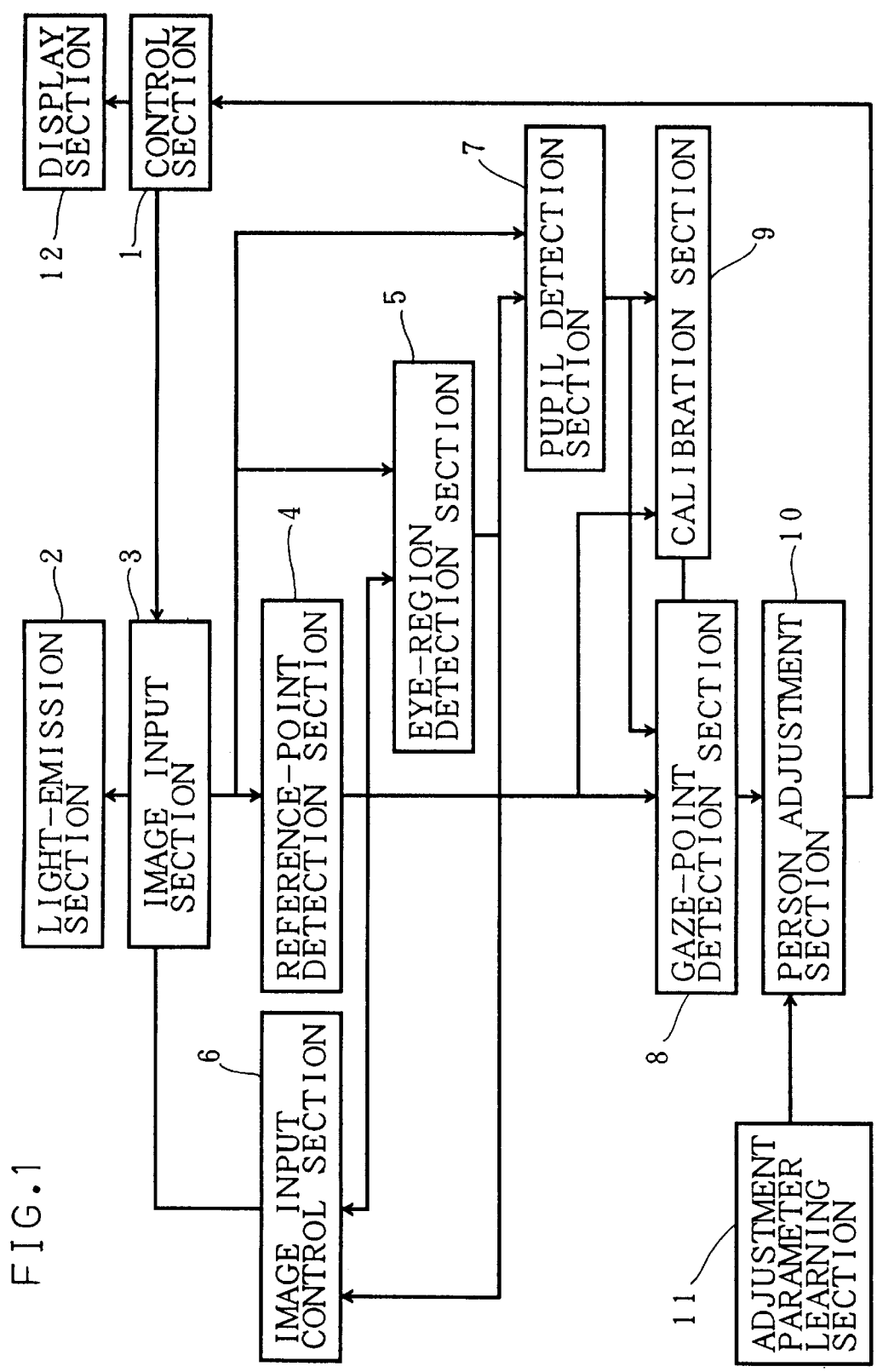
FIG. 1 is a block diagram of a gaze detection apparatus in accordance with a first embodiment.
Figure 2:
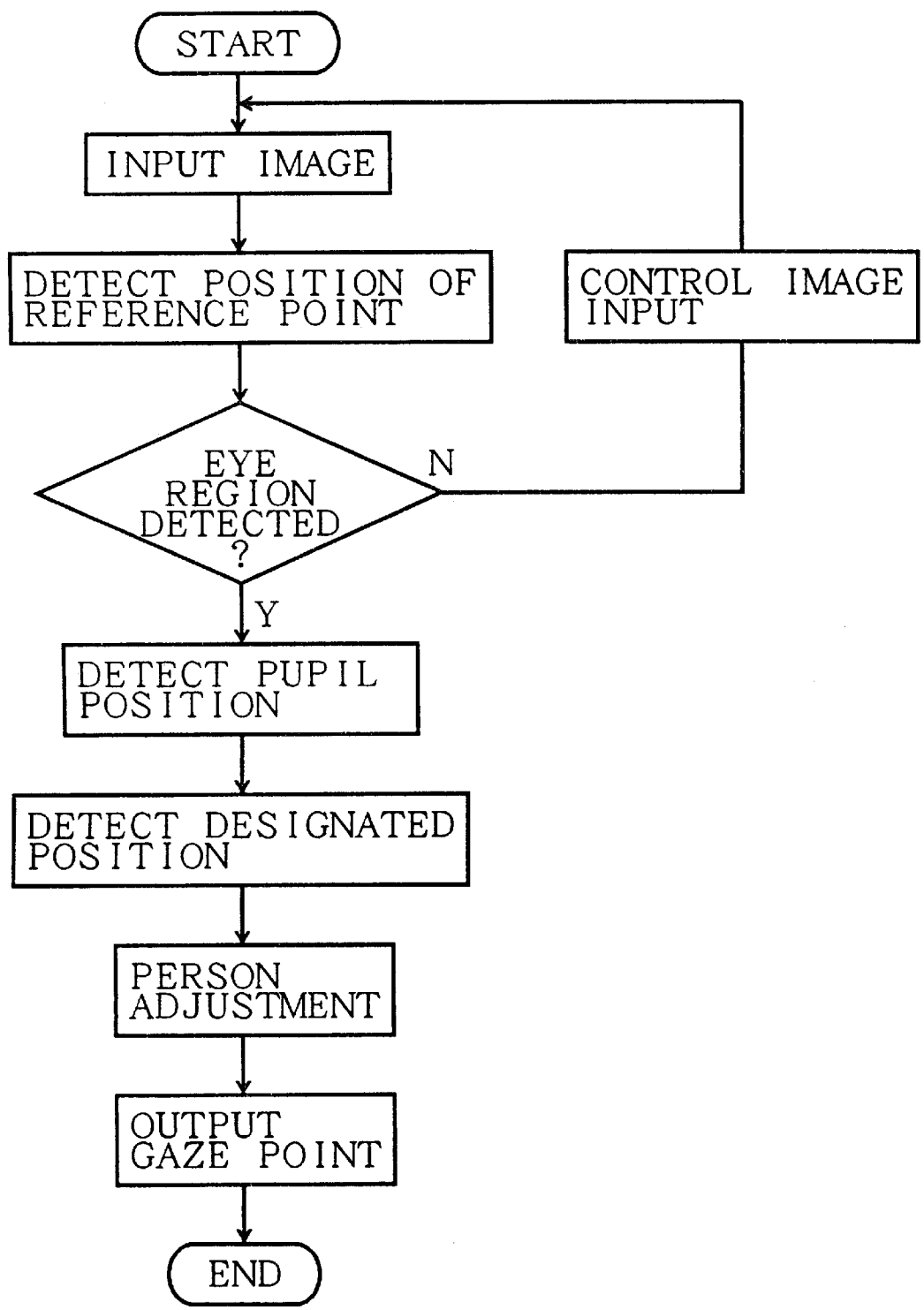
FIG. 2 is a flowchart of the gaze-point information acquisition procedure.

FIG. 1 is a block diagram showing the configuration of a gaze detection apparatus 50 in accordance with the first embodiment. The acquisition procedure of gaze-point information available in this embodiment is shown in FIG. 2.

(Control Section 1)

A control section 1 is connected to receive a user's gaze-point information input request such as depression of a button of a mouse device and a gaze-point information input request from the operating system, application programs or the like, outputting a gaze-point information.

At this time, after reception of such gaze-point information input request, the control section operates as follows: generating a series of control signals for measurement of a gaze point and then outputting the gaze-point information; or alternatively, generating the control signal at fixed time intervals to constantly perform measurement of the gaze point while outputting updated gaze-point information with respect to the gaze-point information upon receipt of such gaze-point information input request.

(Light-Emitting Section 2)

A light-emitting section 2 includes a plurality of light-emitting devices or elements each of which emits light in synchronism with the control signal fed from an image input section 3.

Figure 3:
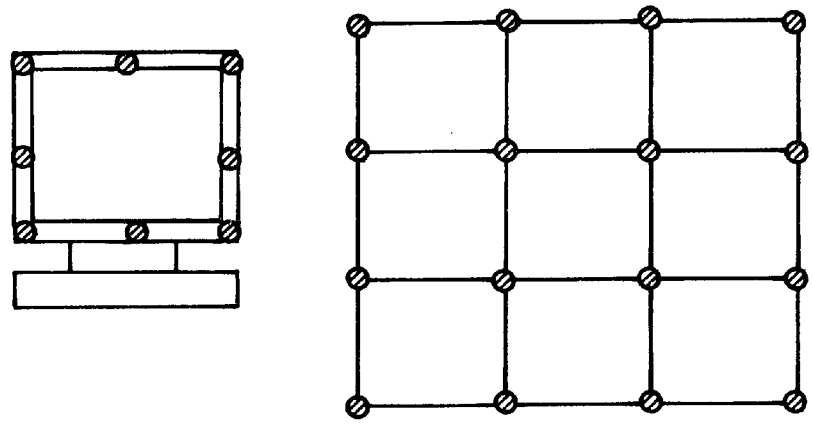
FIG. 3 is an exemplary configuration of a light emitting section.

In the gaze detection apparatus 50 which treats the display plane of a monitor display unit as the user's pointing region (to be referred to as the "object region" hereinafter), the light-emitting elements consist of three or more ones which are disposed on a planar surface that is the same as the display plane of the monitor display as used by the user to make instructions as shown in FIG. 3. In the drawing, portions added with hatching designate the positions of the light-emitting devices.

In the case where the display unit is a device indicated at the left-hand portion of FIG. 3 which employs a cathode-ray tube or Brown tube, the light-emitting devices are disposed at the periphery of the Brown tube as shown.

Where the display unit is a large-size display system called the "video wall" having an assembly of multiple Brown tubes or projection type displays arrayed on a plane, the light-emitting devices are also disposed at or along the joint or "seam" lines between adjacent ones of individual display devices. To avoid dazzling for users' eye, LED elements for emitting infrared light are employed, which are disposed at selected locations shown in FIG. 3. Alternatively, electronic stroboscopic tubes or flash-lights may be used as the light sources in such a manner that light emitted from light source passes through an optical filter for permitting transmission of infrared rays while blocking or absorbing any visible light components thereof and is then guided for illuminance by an optical fiber to reach the position of a corresponding one of the light-emitting elements of FIG. 3. Note that in this example, the displays used are assumed to have a flat surface; however, the display plane may alternatively be curved to some extent.

Figure 4:
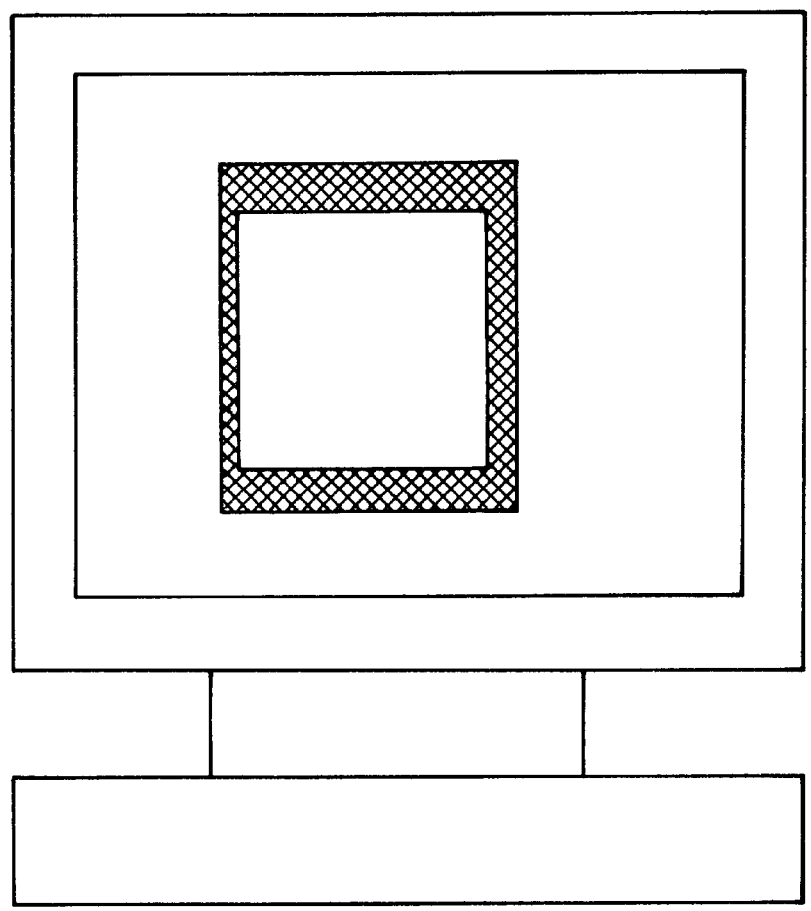
FIG. 4 is an exemplary configuration of the light emitting section using a window frame.

Further, as the light-emitting section 2, display images of a monitor display may also be employed. In this case, two exemplary approaches are available: A plurality of pixels in a small region on the monitor display screen are increased in brightness or luminance; or, pixels within a known-shaped region having a predefined area or greater—such as a presently displayed window frame shown in FIG. 4 in the case of multiwindow displaying—are increased in luminance and used as the light-emitting section which are used in place of the light-emitting device. Where the window frame is used as the light-emitting section, a plurality of window frames are no longer necessary.

(Image Input Section 3)

An image input section 3 is provided for sensing or photographing the eyes of a user by a single TV camera, and for outputting it toward a reference-point detection section 4, eye-region detection section 5 and pupil detection section 7.

First, the image input section 3 supplies a control signal to the light-emitting section 2 for photographing the eyes of the user while the light-emitting section 2 is emitting light. Where the light source is an electronic stroboscopic or flash light device, flash light is to be emitted during photographing of an image.

Next, an image is photographed in the absence of any light from the light-emitting section 2. The order of photographing such two pieces of images is of no care. Additionally, the photographing time points of such two images are shortened in interval; for example, these may be two successive frames at a video rate.

(Reference-Point Detection Section 4)

The reference-point detection section 4 first executes a subtraction processing in such a way as to subtract, with respect to the two images as photographed by the image input section 3, one image photographed in the absence of any light of the light-emitting section 2 from the other image as photographed while the light-emitting section 2 emits light.

In a difference image as a result of the processing, the values of pixels at certain portions whereat the light emitted from the light-emitting section 2 is reflected on the user's eyes are positive in polarity whereas the remaining pixels are equal to approximately zero.

The resulting image of the subtraction processing is then compared with a threshold value for binarization, thus obtaining corresponding binary pixels by extracting therefrom those pixels which are greater than the threshold value.

Every adjacent pixels in resulting image are putted with same label. And, the image is divided into isolated regions.

Thereafter, those having an area falling within a predefined range are extracted letting the coordinates of the center of gravity or "centroid" of each extracted region be regarded as the coordinates of a reference point.

In cases where the gaze-point information is measured continuously, any extra subtraction processing will no longer be required once after completion of detecting the position of each reference point by the above-mentioned subtraction processing. It can be considered that the position and posture of the user's head and the direction of the user's eyes will hardly vary significantly between neighboring ones of the successive images; it is thus possible to continue detecting the coordinates by performing a tracking processing with respect to the reference point(s) as obtained by the prior processing result.

Upon input of the image photographed while the light-emitting section 2 emits light, image binarization and labelling are performed detecting certain region which has an area falling within the predefined range to obtain the centroid coordinates of an extracted region. And, for each reference point, the centroid coordinates, which maximally approximate the reference-point coordinates as detected by the previous processing of the reference-point detection section 4, are then regarded as the reference point coordinates. On occasions where the distance between the reference point coordinates detected by the previous processing and the detected centroid coordinates is greater than a predetermined threshold value, that reference point will not be used in later steps of processing. Also, where the average value, with respect to all the reference points, of the distance between the reference point coordinates detected by the previous processing and the centroid coordinates of the region detected is greater than a predefined fixed value, the reference point coordinates will be calculated using the subtraction processing as mentioned previously.

(Eye-Region Detection Section 5)

An eye-region detection section 5 is provided for inputting the reference point coordinates from the reference-point detection section 4, and for calculating a rectangle which circumscribes the aggregation or "ensemble" of reference points. With the centroid of this rectangle being as the center, an eye region is defined by certain values each of which is a product of the longitudinal or lateral length of such rectangle as multiplied by a predetermined constant value.

(Image Input Control Section 6)

Figure 5:
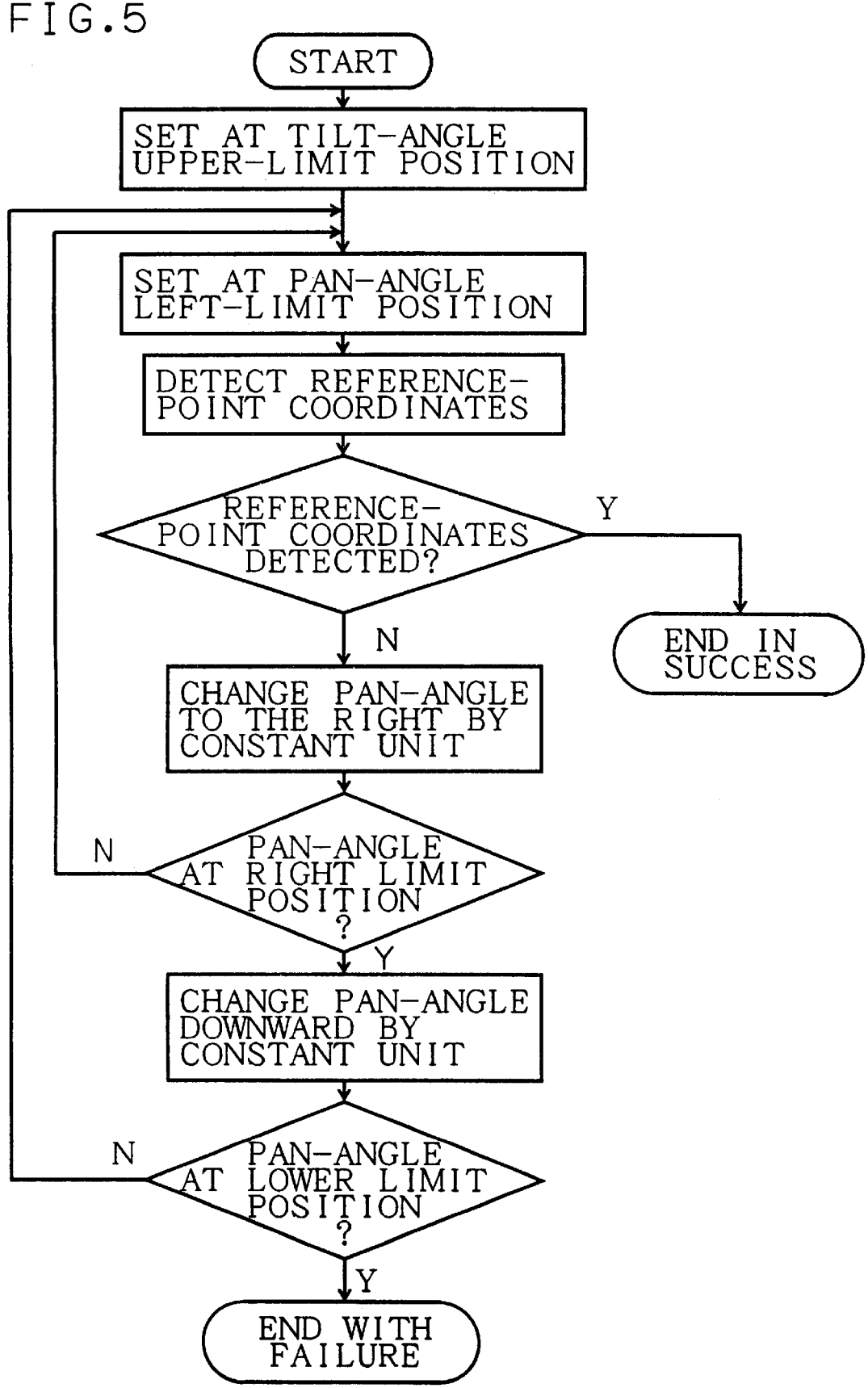
FIG. 5 is a flowchart of camera universal-head control.

An image input control section 6 operates to optimally retain the conditions for photographing the user's eyes by controlling the image input section 3. A single TV camera of the image input section 3 is mounted on a movable/pivotable universal head that may offer several kinds of rotational movements including right- and left-directional rotations (pan) as well as upward and downward rotations (tilt). First, the ensemble of reference points is input from the reference-point detection section 4. If no reference points are found in the input image, then the camera universal head is activated in accordance with a flowchart of FIG. 5 performing detection of one or more reference points while scanning the space that can be photographed by the TV camera.

It should be noted that the reference-point detection is still available even when a target person is moving because the single TV camera is movable as well.

After one or more reference points are detected, the image input control section 6 inputs from the eye-region detection section 5 the center position and area of an eye region. Then, it controls the direction of the TV camera acting as the image input section 3 and the zoom ratio of camera lens in such a way that the eye region is at the center of the image photographed by the image input section 3 while the area falls within a preset fixed range. Additionally, in the case of continuously measuring the gaze-point information, it controls the camera direction such that the centroid of pupil measured by the previous processing is exactly at the center position of the image.

(Pupil Detection Section 7)

Figure 6:
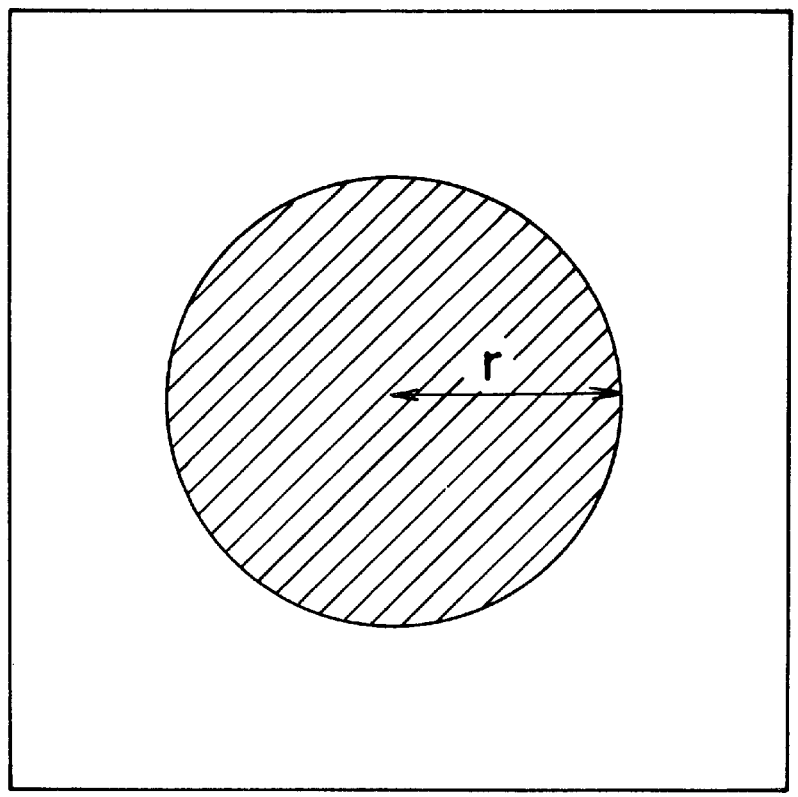
FIG. 6 is a mask image for use in detecting the gaze point.

A pupil detection section 7 detects the pupillar position from the eye region in the image—that is, the position of pupil or iris. This processing starts with a overlay-incorporation processing of the image of eye region and a preset mask image. The mask image used here is shown in FIG. 6, which is an image having pixels of "−1" within a circle of radius r, and pixels of "1" outside the circle.

Next, respective pixel values of resultant overlay-incorporation-processed image are subject to comparison thereby extracting therefrom a specific one having the maximum value.

Figure 7:
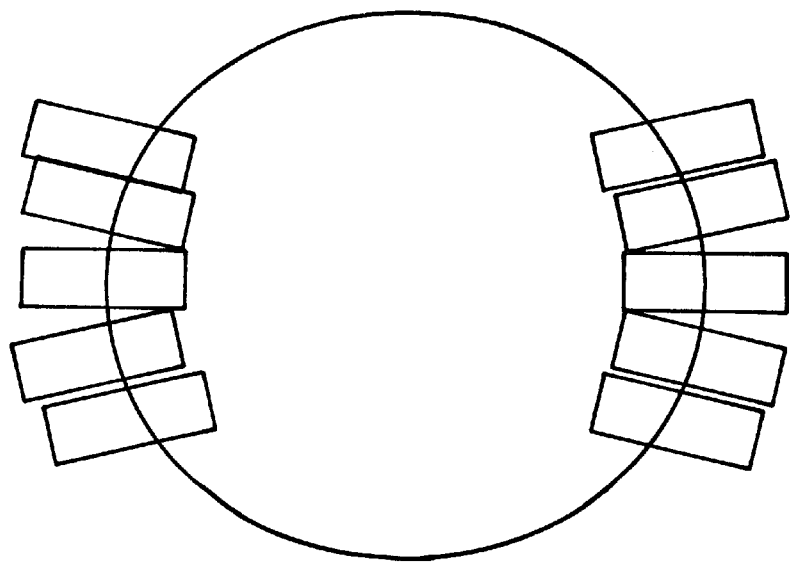
FIG. 7 is a mask image for use in detecting the pupil contour.

With the position of such maximum-value pixel being as the center, ten masks are then disposed on the right- and left-hand sides on the circumference of the circle of radius r as shown in FIG. 7; subsequently, a detection processing is carried out for detecting the so-called "step edge" in the art, which edge partitions the mask area into the inside part of the circle and the outer region thereof. At this time, there remains selectable which one of the pupil and iris is to be an object being detected, by changing the value of r.

Thereafter, an ellipse equation is fitted by least-square estimation with the position coordinates of the total of ten points of edge position information detected within respective masks and the ellipse equation, thus obtaining a specific ellipse that is the nearest to the edge positions of such ten points. The pupil detection section 7 then outputs the centroid coordinates of resultant ellipse as obtained by the above least-square estimation and the longer diameter of the ellipse as well as the shorter diameter thereof.

(Gaze-Point Detection Section 8)

A gaze-point detection section 8 is to execute arithmetic operations using the centroid of each pupil region and the reference point coordinates, obtaining the coordinates of a gaze point in the object regions designated.

In this example, consider that the designated object region is the display screen of a monitor display unit. Let the pupil's centroid coordinates $M=(x_m, y_m)$. Assume that the position of the i-th ($1 \leq i \leq n$) reference point $R_i$ photographed in the image is $(x_i, y_i)$. In possible combinations for selection of three reference points from the assembly of reference points, certain combination is selected which allows a triangle formed by connecting such three reference points to contain M therein. Here, the three points constituting the triangle are represented as $R_a$, $R_b$, $R_c$, respectively.

At this time, the coordinates of each pupil's centroid may be given as:

$$\begin{pmatrix} x_m \\ y_m \end{pmatrix} = \begin{pmatrix} x_a \\ y_a \end{pmatrix} + \begin{pmatrix} x_b - x_a & x_c - x_a \\ y_b - y_a & y_c - y_a \end{pmatrix} \begin{pmatrix} s \\ t \end{pmatrix} \quad (1)$$

where the parameters s, t in the above Equation 1 may be obtained by:

$$\begin{pmatrix} s \\ t \end{pmatrix} = \begin{pmatrix} x_b - x_a & x_c - x_a \\ y_b - y_a & y_c - y_a \end{pmatrix}^{-1} \begin{pmatrix} x_m - x_a \\ y_m - y_a \end{pmatrix} \quad (2)$$

At this time, the gaze point $(X_m, Y_m)$ is determined by use of calibration data $(X_i, Y_i)$ of each reference point Ri what will be described later, as follows:

$$\begin{pmatrix} X_m \\ Y_m \end{pmatrix} = \begin{pmatrix} X_a \\ Y_a \end{pmatrix} + \begin{pmatrix} X_b - X_a & X_c - X_a \\ Y_b - Y_a & Y_c - Y_a \end{pmatrix} \begin{pmatrix} s \\ t \end{pmatrix} \quad (3)$$

Next, a separate calculation scheme will be described. Represent the centroid of the coordinates of all the reference points $R_i$ as $(x_o, y_o)$ If $$\begin{pmatrix} x_0 \\ y_0 \end{pmatrix} = \begin{pmatrix} \frac{\sum_{i=1}^n x_i}{n} \\ \frac{\sum_{i=1}^n y_i}{n} \end{pmatrix}, \quad \begin{matrix} x_i' = x_i - x_0, \; y_i' = y_i - y_0 \\ X_i' = X_i - X_0, \; Y_i' = Y_i - Y_0 \end{matrix} \quad (4)$$

$$x = \begin{pmatrix} x_1' & y_1' \\ x_2' & y_2' \\ \vdots & \vdots \\ x_n' & y_n' \end{pmatrix}, \; X = \begin{pmatrix} X_1' & Y_1' \\ X_2' & Y_2' \\ \vdots & \vdots \\ X_n' & Y_n' \end{pmatrix} \quad (5)$$

then the relation of x and X is defined using a given 2×2 conversion matrix a, as follows:

$$x = Xa, \; a = \begin{pmatrix} a & c \\ b & d \end{pmatrix} \quad (6)$$

This matrix a may be given by using a pseudo-inverse matrix, as follows:

$$a = (X^T X)^{-1} X x \quad (7)$$

The gaze point may be calculated using a from the pupil's centroid, as follows:

$$(X_m, Y_m) = (x'_m y'_m) \begin{pmatrix} a & c \\ b & d \end{pmatrix} \quad (8)$$

It has been described previously that in the light-emitting section 2, the light-emitting elements are disposed on the same plane as the display screen surface; however, in practicing the invention, the display should not always be the flat plane insofar as there are no adverse influences upon images photographed by the camera. Also, it is not always required that the positions of light-emitting elements be exactly on the display plane.

Since the image input section 3 photographs the user's eye balls in a close-up mode, the foregoing calculation scheme assumes that projection of imaging of the light-emitting section 2 onto the image plane photographed by the camera is certain kind of weak through-view projection with lowered transmissivity. This weak through-view projection approximates the center projection that is the actual camera projection; however, according to "THREE-DIMENSIONAL MODEL MATCHING FROM AN UNCONSTRAINED VIEWPOINT", Thompson, D. W. Mundy, J. L., IEEE proceedings of Robotics and Automation, 1987, pp. 208–220, it has been described that the approximation by such weak through-view projection becomes effective if the size of an object to be photographed by the camera is equal to or less than 10% of the distance between the camera and the object. Typically, the distance from the user's eyes to the display is twice the maximum diameter of display screen. Since the human eye balls measure about 15 mm in radius whereas the 15-inch display is 300 mm in lateral width while the eye-to-display distance is 600 mm; accordingly, successful approximation is attainable with the weak through-view projection. In such circumstances, calculate any possible deviation of the light-emitting device positions from the display plane.

Figure 8:
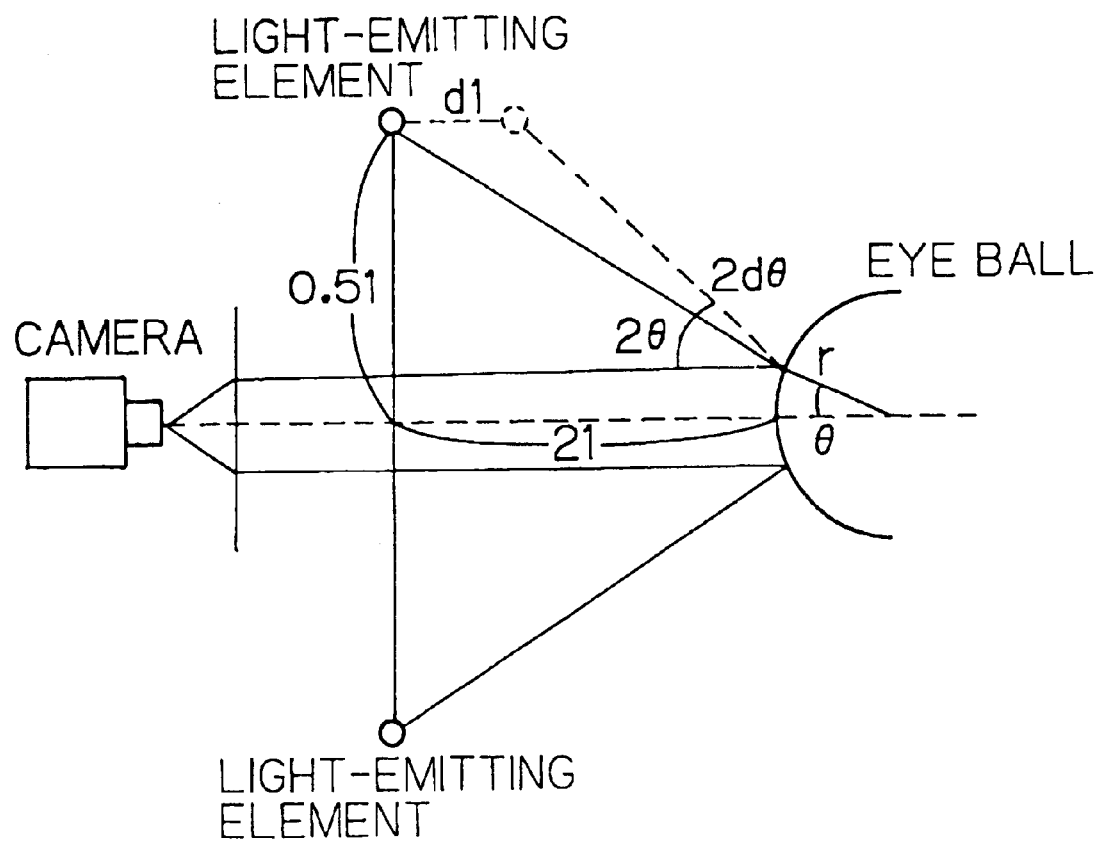
FIG. 8 is a projection of imaging of the light emitting elements.

In the weak through-view projection, it may be approximated that the projection axis from the eye balls to the camera's image-sensing plane is parallel to the optical axis of this camera (FIG. 8). In FIG. 8, the projection position of an imaging of the light-emitting elements disposed at the opposite display edges may be represented by $\gamma \sin(\theta)$ whereas the light-emitting element position is by 21 tan(2θ).

Note here that θ is substantially the same as $\tan^{-1}(0.51/21)$, which is essentially equal to 14 degrees.

Assume that as a result of the position of each light-emitting element being spaced apart by d1 from the display plane, the angle of projection onto the eye balls is deviated by 2dθ.

$$2d\theta = \arctan\left(\frac{0.5l}{2l - dl}\right) - \arctan\left(\frac{0.5l}{2l}\right) \quad (9)$$

Consider that the camera of the image input section 3 is photographing the area of eye balls of 30-mm diameter with the resolution of 500 pixels. In this case, deviation per pixel of reflecting position of light-emitting element on the image may be equivalent to 0.24 degree with dθ being used as deviation of θ. Giving this dθ to the above Equation, d1=0.07 is obtained. In other words, the light-emitting element position will no longer influence on intended measurements as long as the element-to-display distance is within 7% of the display diameter because of the fact that any possible deviation on resultant projected image is less than one pixel.

Accordingly, the light-emitting element position should not exclusively be on the same plane as the display screen. Also, the display screen should not always offer exact flat plane but may be somewhat curved insofar as it is not greater than 7% of the display diameter.

Where the user makes use of glasses on his or her face, it can happen that both the imaging of light emitted from the light-emitting section 2 onto the eyes and imaging of that light on the lenses of glasses are detected at a time at the reference-point detection section 4. This in turn leads to the possibility of occurrence of errors in later processings. To avoid this, the following method is to be employed as follows.

First, where the extracted reference points are greater in number than the light-emitting elements, the reference-point detection section 4 obtains the distance between each reference point and the centroid of all reference points, and then delete a fixed number of reference points sequentially in the order of significance of distance value.

The projection position of an imaging of the light-emitting elements disposed on the periphery of the display onto the camera image is represented by $\gamma \sin(\theta)$. Assuming that the lens surfaces of the glasses exhibit sphere, since the radius $\gamma'$ of this sphere is greater than the eye ball's radius $\gamma$, the reflecting position onto the glasses' lens may distribute over a wide range as compared with that onto the eye balls, resulting in an increase in the distance from the centroid coordinates of all the reference points. Next, after the matrix a of Eq. 6 is obtained, the gaze-point detection section 8 calculates the distance between the calibration data ($X'_i$, $Y'_i$) and the coordinates that is obtained by application of the matrix a to the following reference-point coordinates ($x'_i$, $y'_i$), with respect to each reference point Ri. If there are found certain reference points having a calculated distance greater than a predefined threshold value, then delete such reference points while allowing the remaining ones to be used in re-executing calculation of the matrix a.

At the reference points as obtained from the imaging on the eye balls, Eq. 6 is satisfied. This might ensure that a result of applying the matrix a to the reference-point coordinates is identical to the calibration data in the absence of any measurement tolerance; however, this is not established in the real cases—the result of applying the matrix a to the imaging on the lenses of glasses is not identical to the calibration data. Therefore, any imaging on lenses may be deleted by performing the aforesaid comparison.

(Calibration Section 9)

Figure 9:
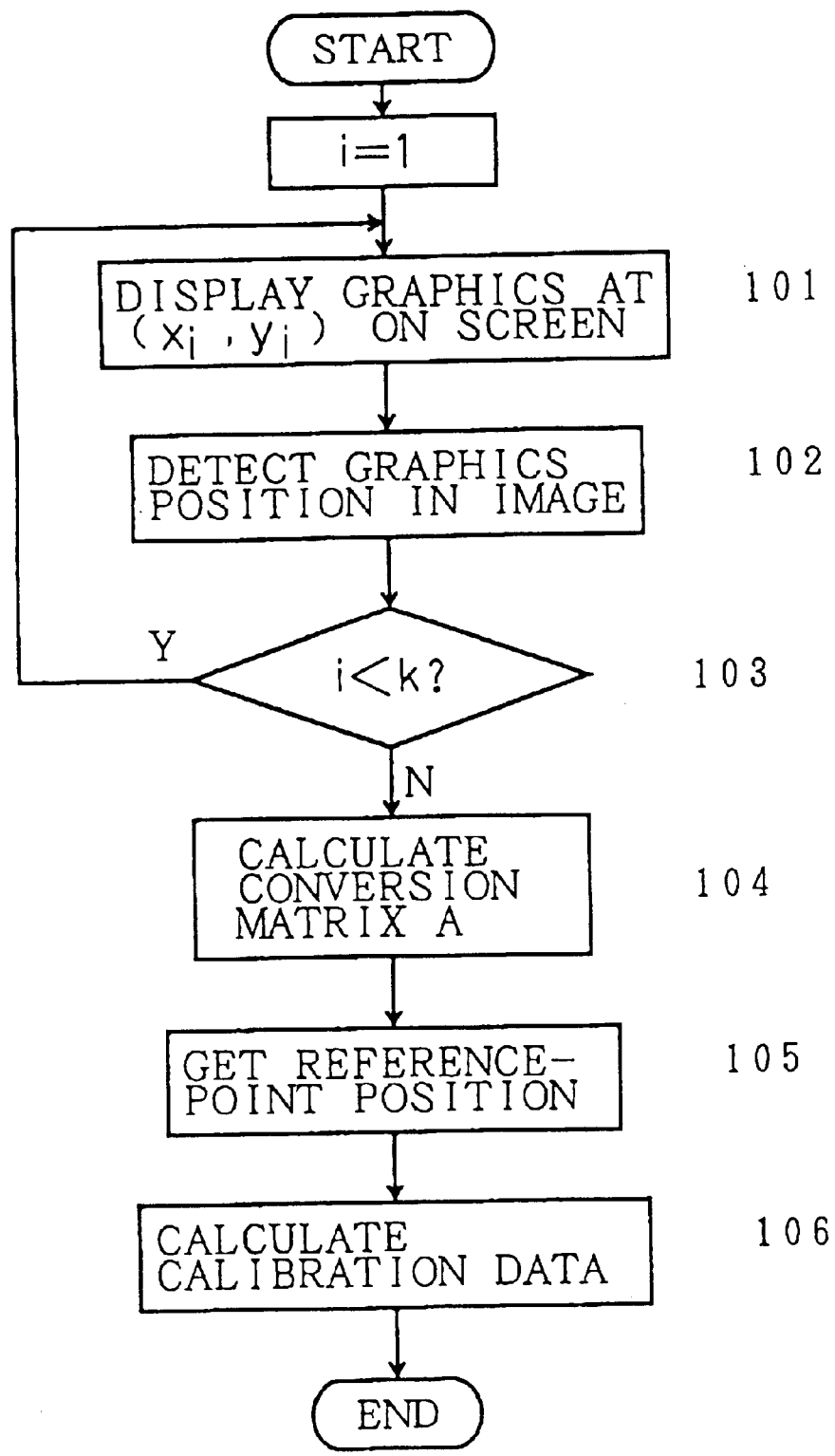
FIG. 9 is a flowchart of calibration procedure.

A calibration section 9 operates to learn some parameters for use in calculating the gaze point and store therein such parameters. FIG. 9 is a flowchart of this calibration.

First, put a mirror at a selected position in front of the display at which position an image of each light-emitting element is projected onto the image as input by the image input section 3.

Display a graphics pattern at predefined coordinates ($X_i$, $Y_i$) on the display screen. For example, display a white-paint circle at the coordinates ($X_i$, $Y_i$) with the entire surface of the screen darkened (at step 101).

Detect from an image photographed by the camera the position ($x_i$, $y_i$) of displayed graphics pattern, in the image (step 102).

Detection is carried out by performing a subtraction processing between the photographed image and the prior image obtained with the entire display screen darkened, binarizing and labelling resultant subtracted image using a fixed threshold value, extracting certain regions each having a value greater than the threshold value, and determining the centroid of a specific region having a maximal area as the position of displayed graphics pattern in the image. By changing the position of the coordinates for displaying on the display screen, the above processings will be repeated a predetermined number (here, k) of times (step 103).

For the position ($X_i$, $Y_i$) on the display and the position ($x_i$, $y_i$) in the image, of the graphics pattern being displayed with respect to k pieces of images, the following relation is established:

$$X = xa, \text{ but } X = \begin{pmatrix} X_1 & Y_1 \\ \vdots & \vdots \\ X_k & Y_k \end{pmatrix}, x = \begin{pmatrix} x_1 & y_1 & 1 \\ x_2 & y_2 & 1 \\ \vdots & \vdots & \vdots \\ x_k & y_k & 1 \end{pmatrix}, a = \begin{pmatrix} a & d \\ b & e \\ c & f \end{pmatrix} \quad (10)$$

From the above equation, calculate the matrix a (step 104).

The matrix a may be given using a pseudo-inverse matrix as follows:

$$a = (X^T X)^{-1} Xx \quad (11)$$

Next, let the reference-point detection section 4 calculate the reference-point position ($x_{ri}$, $y_{ri}$) in the image (step 105).

Use the detected coordinates and matrix a to calculate the calibration data ($X_{ri}$, $Y_{ri}$) of reference points as follows (step 106):

$$\begin{pmatrix} X_{ri} \\ Y_{ri} \end{pmatrix} = \begin{pmatrix} x_{ri} \\ y_{ri} \end{pmatrix} a \quad (12)$$

The calibration data obtained by the above processing may be once determined when the light-emitting section 2 is disposed with the initial settings; accordingly, the calibration data is prepared using the calibration section 9 when the gaze detection apparatus 50 is assembled or when apparatus 50 is attached to the display unit.

(Person Adjustment Section 10)

A person adjustment section 10 will now be described.

The human's eyes are not exactly the true circles. The position of an optical light-axis center may also be different among individuals causing deviation from the center of pupil. For these reasons, the gaze point detected by the gaze-point detection section 8 is a mere gaze point measured from an image as input through the image input section 3, which can differ from the user's intended gaze point in some cases.

The person adjustment section 10 is the unit which adjusts the system output to match the individual characteristics. To do this, the person adjustment section learns some parameters for conversion of an output of the gaze-point detection section 8 into the user's intended gaze point, and then converts the output of gaze-point detection section by using the parameters for adjustment of the system output.

Regarding differences among individual systems such as a difference in position of the light-emitting section 2, the calibration section 9 measures and learns the same. The person adjustment section 10 attempts to learn for adjustment any possible differences among individual users. In this way, preparing the two units—namely, the calibration section 9 for learning system differences, and the person adjustment section for learning influences as to the human's individual differences—enables each user, once the individual differences have been studied and even after the system is modified, to perform gaze point-based positional instructions by using the calibration data of a new system and his or her own individual adjustment parameters.

Figure 10:
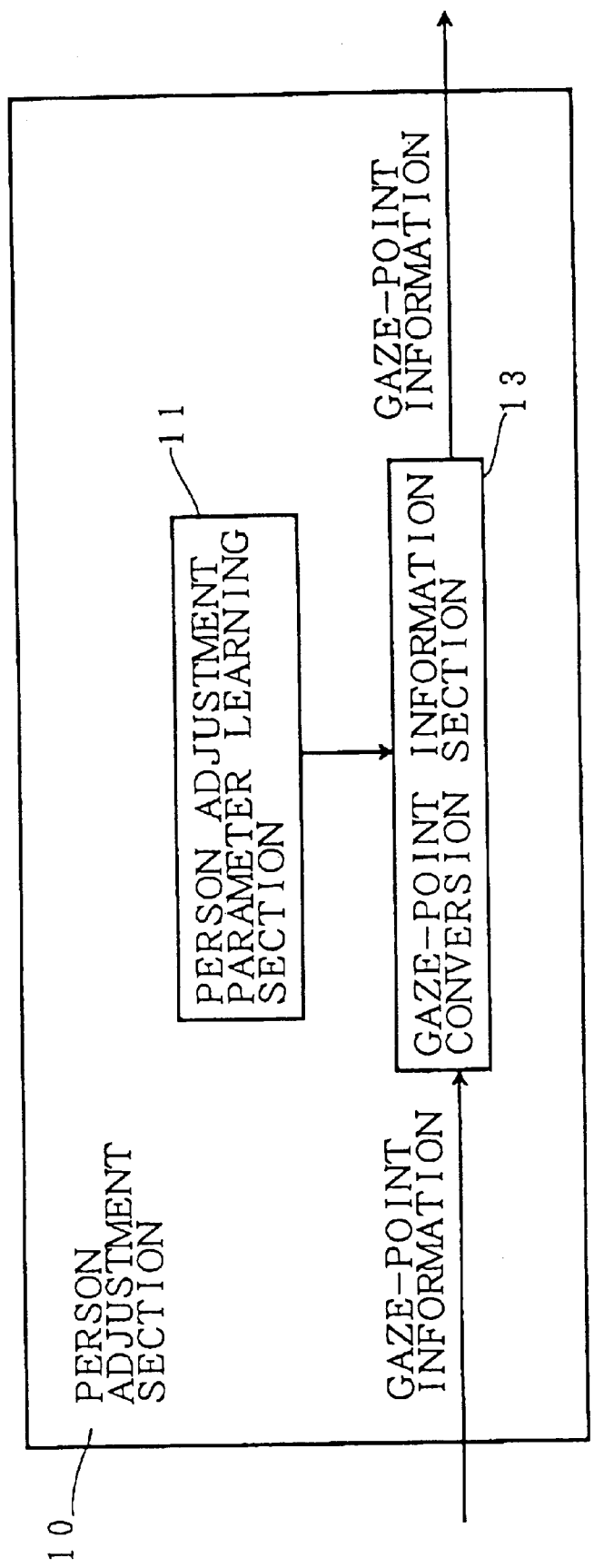
FIG. 10 is a diagram showing a configuration of an individual adjustment section.

A configuration of the person adjustment section 10 is shown in FIG. 10.

The person adjustment parameter learning section 11 acts to display a graphics pattern that will actually become an indicated object on the display, gives correspondence between an output of the gaze-point detection section 8 when the user gazes at this graphics pattern and the display position of the graphics pattern, and learn conversion parameters for converting an output of the gaze-point detection section 8 into the user's intended gaze point. A gaze-point information conversion section 13 makes use of the parameters learned by a person adjustment parameter learning section 11, outputting converted information which is converted from input gaze-point information.

Figure 11:
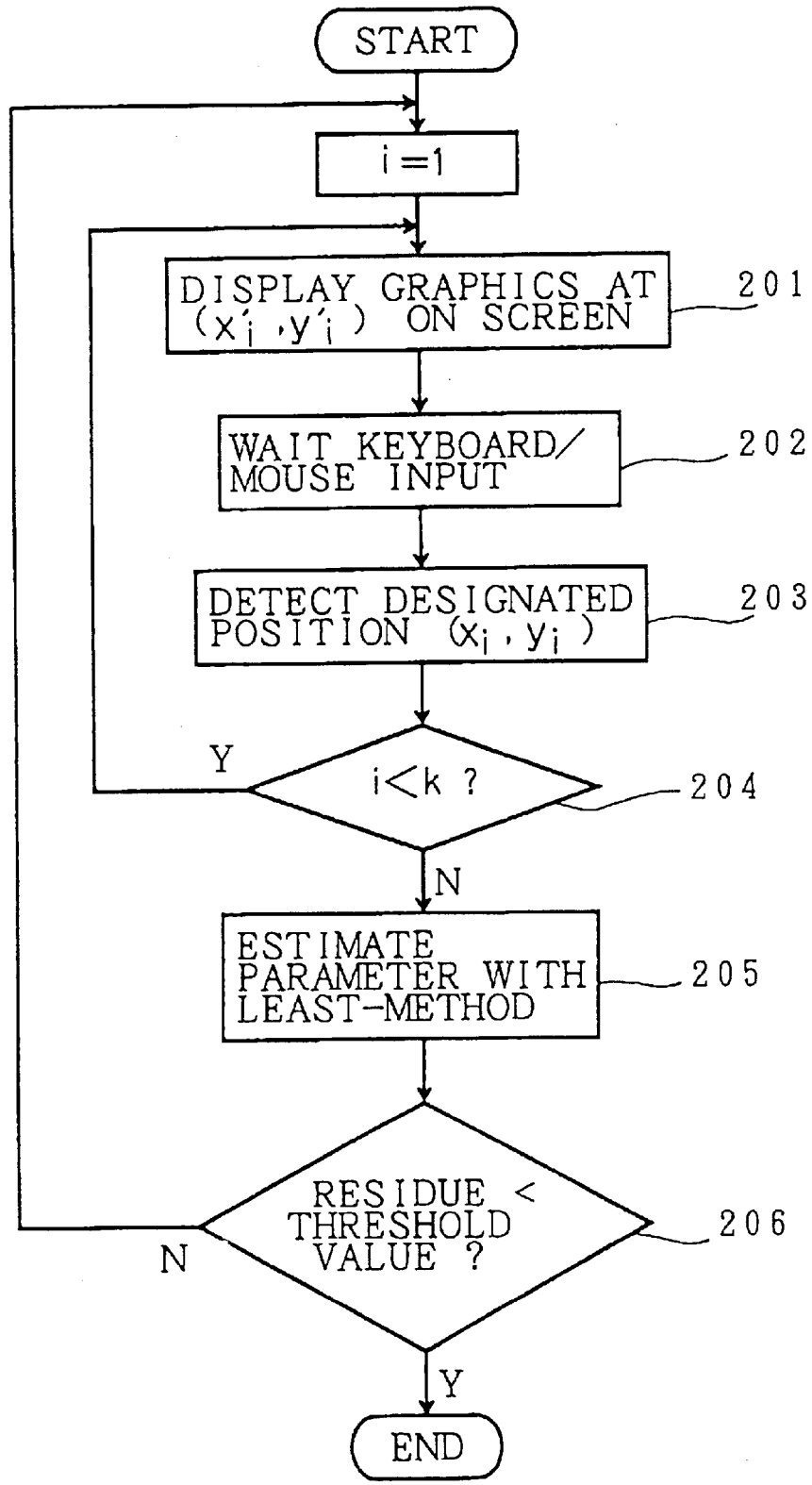
FIG. 11 is a flowchart (1) of an individual adjustment parameter learning section.

A flow of processings in the person adjustment parameter learning section 11 is shown in FIG. 11.

First, display a graphics pattern at each of the predefined positions ($x'_i$, $y'_i$) on the display screen. Such display positions are to be uniformly distributed over the screen (step 201).

While gazing one of the graphics patterns displayed, the user depresses a key on the keyboard, a button of an associated mouse device, or the like. The person adjustment section 10 waits for detection of an input of the keyboard or mouse (step 202).

After completion of the above step, input from the gaze-point detection section 8 the gaze point ($x_i$, $y_i$) by the user's view line (step 203).

Repeat the steps 201 to 203 until the number of gaze points is equal to a fixed number k (step 204).

Next, perform least-square estimation for applying a model that is represented by the following equation with respect to the display positions ($x'_i$, $y'_i$) on the screen and the gaze points ($x_i$, $y_i$) by the user's view line. In the following equation, the number n is a predetermined number such as 2 (step 205).

$$x'_i = \sum_{j=0}^{n} a_j x_i^j + \sum_{j=n+1}^{2n} a_j y_i^j + \varepsilon, \quad y'_i = \sum_{j=0}^{n} b_j x_i^j + \sum_{j=n+1}^{2n} b_j y_i^j + \varepsilon \quad (13)$$

In the least-square estimation, the term $a_j$ (j=0, . . . , n) of parameters $a_j$, $b_j$ (j=0, . . . , n) may be given as a solution of the equation which follows:

$$\begin{pmatrix} k & \Sigma x_i & \cdots & \Sigma x_i^n & \Sigma y_i & \cdots & \Sigma y_i^n \\ \Sigma x_i & \Sigma x_i^2 & \cdots & \Sigma x_i^{n+1} & \Sigma x_i y_i & \cdots & \Sigma x_i y_i^n \\ \vdots & \vdots & \vdots & & \vdots & & \\ \Sigma x_i^n & \Sigma x_i^{n+1} & \cdots & \Sigma x_i^{2n} & \Sigma x_i^n y_i & \cdots & \Sigma x_i^n y_i^n \\ \Sigma y_i & \Sigma x_i y_i & \cdots & \Sigma x_i^n y_i & \Sigma y_i^2 & \cdots & \Sigma y_i^{n+1} \\ \vdots & \vdots & \vdots & & \vdots & & \\ \Sigma y_i^n & \Sigma x_i y_i^n & \cdots & \Sigma x_i^n y_i^n & \Sigma y_i^{n+1} & \cdots & \Sigma y_i^{2n} \end{pmatrix} \begin{pmatrix} a_0 \\ a_1 \\ \vdots \\ a_n \\ b_1 \\ \vdots \\ b_n \end{pmatrix} = \begin{pmatrix} \Sigma x'_i \\ \Sigma x_i x'_i \\ \vdots \\ \Sigma x_i^n x'_i \\ \Sigma y_i x'_i \\ \vdots \\ \Sigma y_i^n x'_i \end{pmatrix} \quad (14)$$

Regarding the parameter $b_j$ (j=0, . . . , n) also, it may be calculated as the solution of the same equation as in the case of $a_j$.

Then, compare the residual difference average obtained by the least-square estimation at the step 205 with a predetermined threshold value (step 206). If the residual difference average is less than the threshold value, then output resultant parameters $a_j$, $b_j$ (j=0, . . . , n) obtained by the least-square estimation to the person adjustment section 10, as the learning parameters.

If the residual difference average obtained least-square estimation is greater than the predetermined threshold value then repeat the processings following the step 201.

Figure 12:
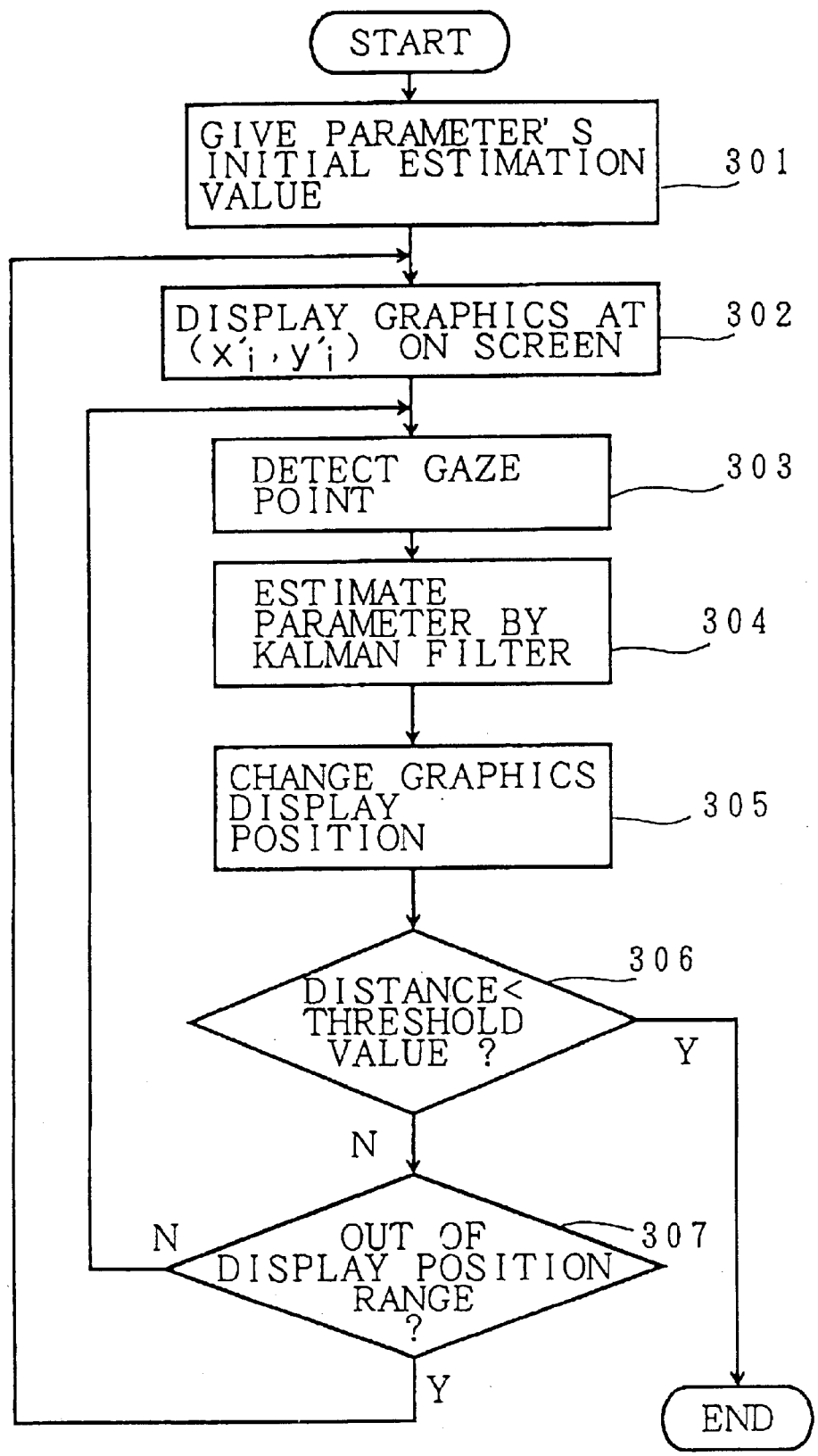
FIG. 12 is a flowchart (2) of the individual adjustment parameter learning section.

Next, another exemplary configuration of the person adjustment parameter study section 11 is shown in FIG. 12. Assume here that the display positions ($x'_i$, $y'_i$) on the display screen offer a specific relation with respect to the gaze points ($x_i$, $y_i$) by the user's view line which is defined by the following equation. The number n in this equation is a predefined number, such as 2.

$$x'_i = \sum_{j=0}^{n} a_j x_i^j + \sum_{j=n+1}^{2n} a_j y_i^j, \quad y'_i = \sum_{j=0}^{n} b_j x_i^j + \sum_{j=n+1}^{2n} b_j y_i^j \quad (15)$$

First, as the initial estimation values of the parameters $a_j$, $b_j$ (j=0, . . . , n), let $a_1$=1, $b_1$=1 with the remaining parameters being at zero (step 301).

Display a graphics pattern at each of the predefined positions ($x'_i$, $y'_i$) on the screen, allowing the operator to look at or gaze any desired one of such graphics patterns displayed (step 302).

Input from the gaze-point detection section 8 a gaze point ($x_i$, $y_i$) indicated by view line (step 303).

Perform estimation of the $a_j$, $b_j$ (j=0, . . . , n) from the positions ($x_i$, $y_i$) and ($x'_i$, $y'_i$) (at step 304). For this parameter estimation, the Kalman filter scheme may be employed which has been disclosed, for example, in "Digital Signal Processing and Control", by Hideki Kimura at p. 212.

The Kalman filter is an algorithm for estimation of the state vector x[t] based on measurement data y[t] in a model that is represented by the following equation:

$$x[t+1]=A[t]x[t]+B[t]v[t]y[t]=C[t]x[t]+w[t] \quad (16)$$

v[t] is the white Gaussian process of covariance matrix Q[t]

w[t] is the white Gaussian process of covariance matrix R[t]

For the position ($x'_i$, $y'_i$) of the t-th graphics pattern on the display screen and the gaze point position ($x_t$, $y_t$) input from the gaze-point detection section 8, the state vector x[t] representative of the parameters $a_j$, $b_j$ (j=0, . . . , n) may be represented as:

$$x[t]=(a_0[t], \ldots, a_{2n}[t], b_0[t], \ldots, b_{2n}[t])^T \quad (17)$$

Also, the transition matrix A, measurement matrix C, and observation data y[t] are given by:

$$A = \begin{pmatrix} 1 & 0 & \cdots & 0 \\ 0 & 1 & \cdots & 0 \\ 0 & 0 & \cdots & 1 \end{pmatrix}, \quad y = \begin{pmatrix} x'_t \\ y'_t \end{pmatrix}$$

$$C[t] = \begin{pmatrix} 1 & x_t & \cdots & x_t^n & y_t & y_t^n & 0 & \cdots & \cdots & \cdots & \cdots & 0 \\ 0 & \cdots & \cdots & \cdots & \cdots & 0 & 1 & x_t & x_t^n & y_t & \cdots & y_t^n \end{pmatrix}$$

The state vector estimation is carried out by use of the above matrix representations. A predetermined fixed matrix is given to the covariance matrixes Q[t], R[t] of tolerance for use in estimation.

Next, use the matrix C[t] which is obtained from the estimated state vector x and the output ($x_y$, $y_t$) of the gaze-point detection section 8 to modify the graphics display position ($x'_t$, $y'_t$) as follows (step 305):

$$y=Cx \quad (18)$$

Determine whether the distance between the previous display position and a newly estimated position is less than the predetermined threshold value: If it is less than the threshold value then the processing is terminated (step 306).

Determine if such new estimated position is out of the displayable range of the display unit: If it is within the range then display a graphics pattern and repeat the processings following the step 302. If the estimated position is out of the displayable range then reset the display position at the initial value for repeating the processings following the step 301 (step 307).

Figure 13:
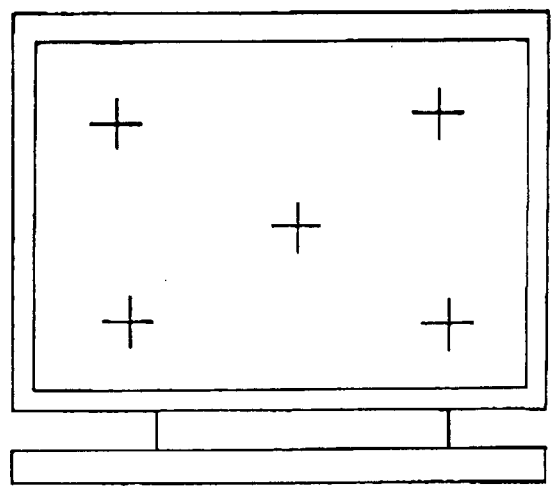
FIG. 13 is an example of the graphics display position.

The foregoing processings will be performed several times while modifying the initial value-displaying position on the display screen. For example, sequentially modify the initial position for displaying graphics on the display screen among five locations shown in FIG. 13; while starting from each initial position, terminate the learning of person adjustment parameters instantly when the processing of the step is terminated, thereby outputting resultant parameters $a_j$, $b_j$ (j=0, . . . , n) to the person adjustment section 10.

Incidentally, one prior known apparatus for detecting the user's gaze point from an image photographed by a camera has been proposed in JPA 02134130. This apparatus is designed to detect from the image both the center of eye ball and the center of pupil, then detecting a straight line coupling between the both as a view line.

However, with this apparatus, it merely detects a projection of the view line in the 3D-space onto the camera's 2D-photographing plane; it remains incapable of identifying the position of an object indicated by the view line in the 3D-space.

It has also been proposed that this apparatus detects a gaze point in 3D-space using two cameras based on the principle of stereoscopic measurement.

However, since such stereoscopic measurement inherently requires increased accuracy for execution of calibration processing of the positional relation between the cameras used, the accuracy of detection will decrease on occasions where certain kinds of operations are performed which include camera rotation and zooming.

Furthermore, when a gaze point is obtained on the object to be indicated, it is required that the view line detected in the camera coordinate system be subject to specific coordinate conversion to the object coordinate system with the object to be indicated being as the center, by use of the positional relationship between the cameras and the indicated object.

In contrast, with the present embodiment, the coordinates of a gaze point are directly measured within the image by disposing three or more light-emitting points near or around such gaze point. For this reason, even where certain operations including camera rotation and zooming as in the apparatus of JPA 02134130, the detection accuracy will no longer decrease without the need to do any coordinate conversion processing from the camera coordinate system to the object coordinate system.

Second Embodiment

An exemplary arrangement of the second embodiment will now be described. In this example, the apparatus is different from that of FIG. 1 in the gaze-point detection section 8, person adjustment section 10 and person adjustment parameter learning section 11.

(Gaze-Point Detection Section 8)

A configuration of the gaze-point detection section 8 will first be described.

Assume that the coordinates of the centroid of input pupil is $M=(x_m, y_m)$. Let the position of the i-th (1<=i<=n) reference point Ri photographed in the image be expressed as $(x_i, y_i)$ while representing the calibration data as $(X_i, Y_i)$.

In Eq. 10, calculate the matrix a for conversion of $(x_i, y_i)$ into $(X_i, Y_i)$. In regard to an image I having a fixed size with the centroid of pupil being as the center thereof, the brightness of one pixel at the position (x, y) is represented by I(x, y). Under this condition, perform mapping an image which was subjected to the affine conversion or transformation represented by the matrix a. As a result of such affine transformation, the image I is projected onto another image I' by the following equation. Since none of the calibration data $(X_i, Y_i)$ vary depending upon images converted, the light-emitting section 2 at the position $(x_i, y_i)$ prior to such projection will be projected without exceptions at the position of the calibration data $(X_i, Y_i)$.

$$I'(ax+by+c, dx+ey+f) = I(x,y) \qquad (19)$$

Figure 14:
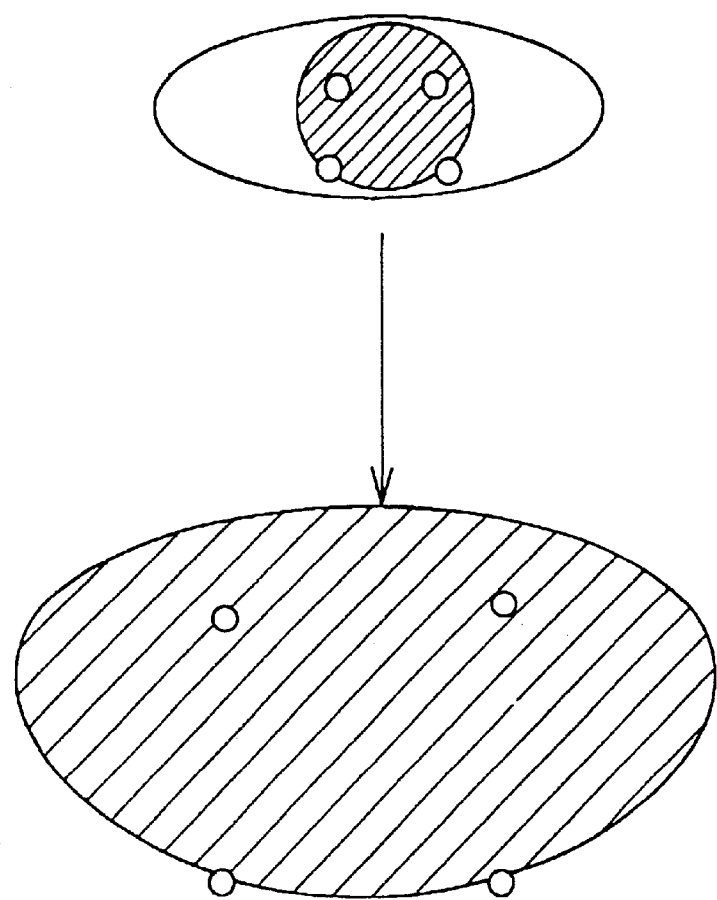
FIG. 14 is an example of affine image.
Figure 15:
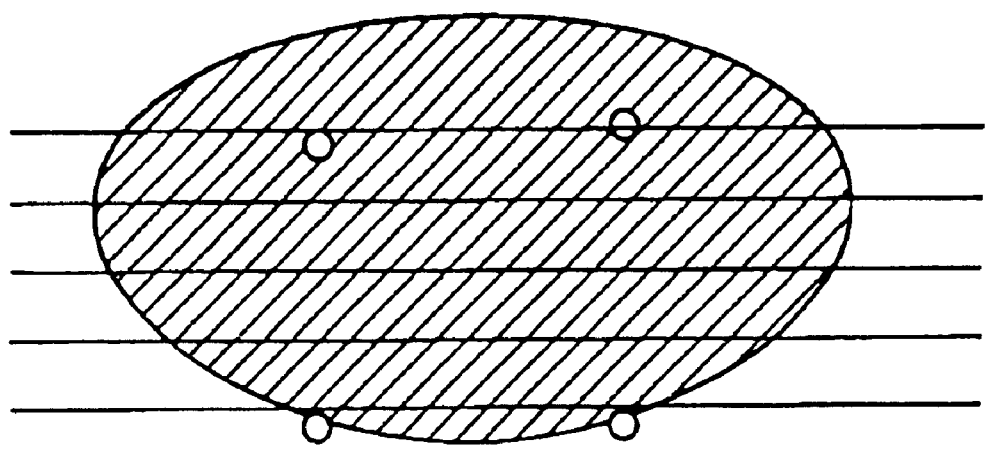
FIG. 15 is edge detection positions.

One example of the affine-mapped image is shown in FIG. 14. In the mapped image, edge extraction is performed on a predetermined straight line defining the position of each contour edge of a pupil image thus projected. FIG. 15 is one example of straight line for executing edge extraction by the aforesaid method. Edge extraction is carried out on this straight line. For such edge extraction, first perform overlay-incorporation arithmetic operations of an extraction filter having a step-like edge with pixels on the straight line expressed as I(x). Then, extract a local maximal value from a overlay-incorporation result; extract therefrom certain values greater than the predetermined threshold value. If any values greater than the threshold value are found then define as the edge positions the position whereat the edge filter exhibits the maximum value and the position whereat it exhibits a second largest value.

The gaze-point detection section 8 outputs to the person adjustment section 10 the edge position(s) on a respective one of the straight lines.

(Person Adjustment Section 10)

The person adjustment section 10 performs conversion of an output of the gaze-point detection section 8 into the user's intended gaze point by use of the parameters that the person adjustment parameter learning section 11 has learned. Assume here that there are n straight lines for execution of edge extraction in the gaze-point detection section 8. Represent the positions of an edge input from the i-th straight line as $x_{1i}$, $x_{ri}$. Calculate output gaze point $(x_p, y_p)$ at this time, as follows:

$$\begin{pmatrix} x_p \\ y_p \end{pmatrix} = \begin{pmatrix} \sum_{i=0}^{n-1} a_i x_{li} + \sum_{i=0}^{n-1} a_{n+i} x_{ri} \\ \sum_{i=0}^{n-1} b_i x_{li} + \sum_{i=0}^{n-1} b_{n+i} x_{ri} \end{pmatrix} \qquad (20)$$

The parameters $a_j$, $b_j$ (j=0, . . . , 2n) to be used for this calculation may be obtained from the person adjustment parameter study section.

(Person Adjustment Parameter Learning Section 11)

The person adjustment parameter learning section 11 operates to display a graphics pattern being actually indicated on the display screen, give correspondence between an output of the gaze-point detection section 8 and the display position of such graphics when the user gazes at this graphics, and learn the conversion parameters for converting the output of the gaze-point detection section 8 into the user's intended gaze point.

A flow of procedure of this person adjustment parameter study section 11 is similar to that previously explained with reference to FIG. 12; accordingly, an explanation here also uses this drawing.

First, as the initial estimation values of the parameters $a_j$, $b_j$ (j=0, . . . , 2n), set $a_i=1$, $b_i=1$ with the remaining parameters being at zero (step 301).

Display a graphics pattern at each of the predefined positions $(x'_i, y'_i)$ on the screen, allowing the user to gaze any desired one of such graphics patterns displayed (step 302).

Input from the gaze-point detection section 8 the edge position $x_{li}$, $x_{ri}$ (i=1, . . . , n) (step 303).

Perform estimation of the $a_j$, $b_j$ (j=0, . . . , 2n) from the edge position $x_{1i}$, $X_{ri}$ (i=1, . . . n) and the graphics positions $(x'_i, y'_i)$ by use of the Kalman filter method in the same manner as in the step 304 in the first embodiment described above (step 304).

For the position $(x'_t, y'_t)$ of the t-th graphics pattern on the display screen and the edge position $x_{li}$, $x_{ri}$ as input from the gaze-point detection section 8, the state vector $x[t]$ representative of the parameters $a_j$, $b_j$ (j=0, ..., 2n) may be represented by:

$$x[t] = (a_0[t], \ldots, a_{2n}[t], b_0[t], \ldots, b_{2n}[t])^T \quad (21)$$

Also, the transition matrix A, measurement matrix C, and observation data y[t] are given as follows:

$$A = \begin{pmatrix} 1 & 0 & \cdots & 0 \\ 0 & 1 & \cdots & 0 \\ 0 & 0 & \cdots & 1 \end{pmatrix}, \quad y = \begin{pmatrix} x'_t \\ y'_t \end{pmatrix}$$

$$C[t] = \begin{pmatrix} x_{ll} & x_{rl} & \cdots & x_{ln} & x_m & 0 & \cdots & \cdots & \cdots & 0 \\ 0 & \cdots & \cdots & \cdots & 0 & x_{ll} & x_{rl} & \cdots & x_{ln} & x_m \end{pmatrix}$$

The state vector estimation is carried out by use of the above matrix representations. Regarding the covariance matrixes Q[t], R[t] of tolerance for use in estimation, a predetermined fixed matrix is given to Q[t], whereas an appropriate matrix is given to R[t] depending upon the reliability of edge extraction result of a corresponding edge position $x_{li}$ or $x_{ri}$.

Next, use the matrix C[t] obtained from the estimated state vector x and the output $x_{li}$, $x_{ri}$ (i=1, ..., n) of the gaze-point detection section 8 to calculate the next graphics' position $(x'_t, y'_t)$ as follows (step 305):

$$y = Cx \quad (22)$$

Determine whether the distance between the previous display position and a newly estimated position is less than the predetermined threshold value: If it is less than the threshold value then terminate the processing (step 306).

Determine whether such new estimated position is out of the displayable range of the display unit: If it is within the range then display a graphics pattern and repeat the processings following the step 302. If the estimated position is out of the displayable range then reset the display position at the initial value to repeat the processings following the step 301 (step 307).

If the distance is less than the predetermined threshold value then perform again the above processings while changing the position for displaying the initial value on the display screen. For example, sequentially modify the initial position for displaying graphics on the screen among five locations shown in FIG. 13; while starting from each initial position, terminate the study of person adjustment parameters when the processing of the step is terminated; and then, outputting resultant parameters $a_j$, $b_j$ (j=0, ..., 2n) to the person adjustment section 10.

Third Embodiment

A description will now be given of an information selection apparatus 110 in accordance with one embodiment of the present invention. This embodiment assumes that the information selection apparatus 110 is implemented in vending machines, ticket selling machines or the like. Note that the term "system" as used herein refers to apparatus including such vending machines, ticket machines or the like.

Figure 16:
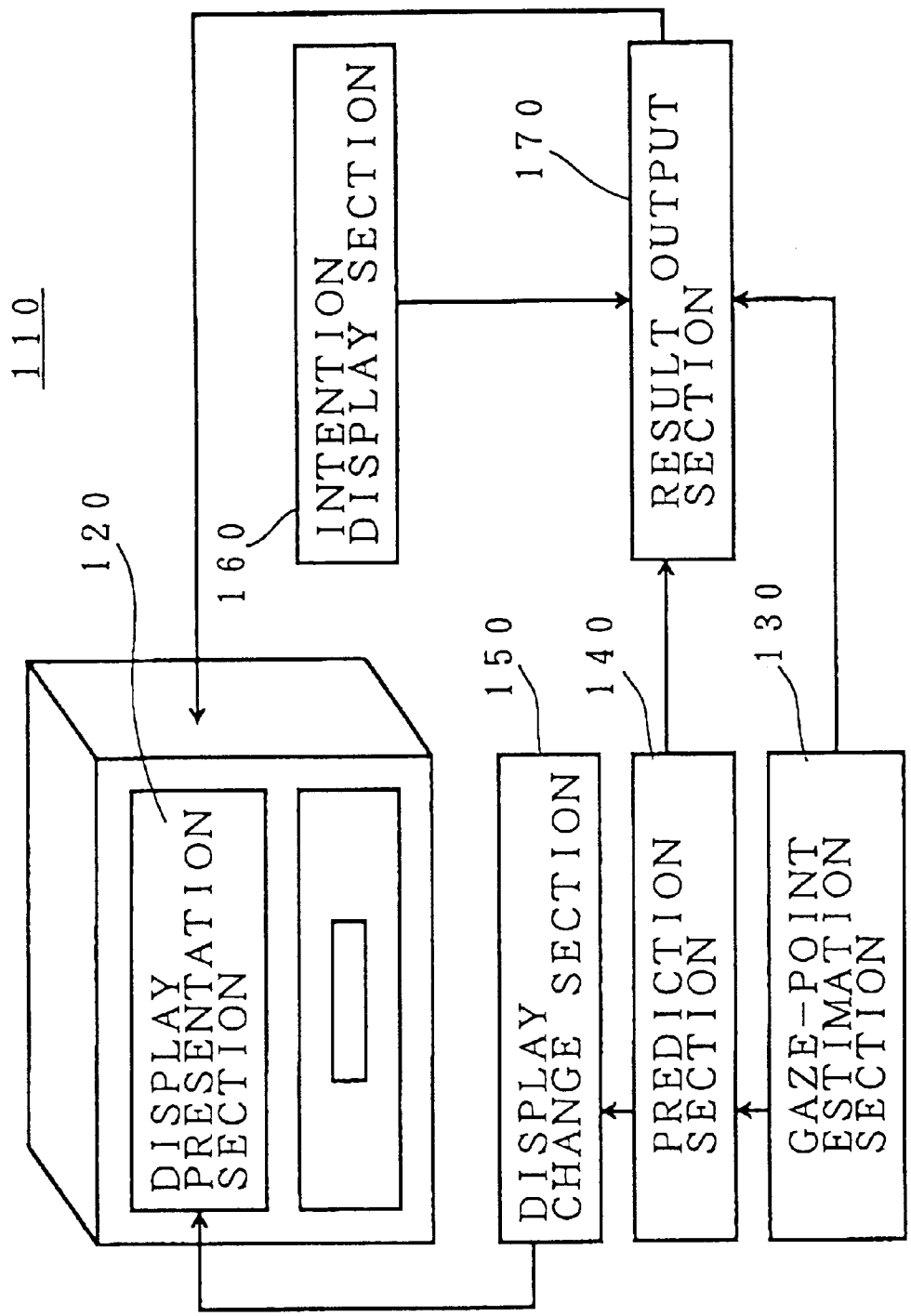
FIG. 16 is a block diagram of apparatus.

A block diagram of the information selection apparatus 110 is shown in FIG. 16.

The information selection apparatus 110 is generally constituted from an information presentation section 120 such as a display, CRT, liquid crystal display panel, sign board, display plate or the like, a gaze-point detection section 130 for detecting the user's gaze point, a prediction section 140 for prediction of the user's selection content(s), a display change section 150 for changing or updating the display contents, an intention transmission section 160 for permitting input of a signal(s) from the user or the inside of the system, and a result output section 170 for retaining a selection result.

Information Presentation Section 120

Figure 17:
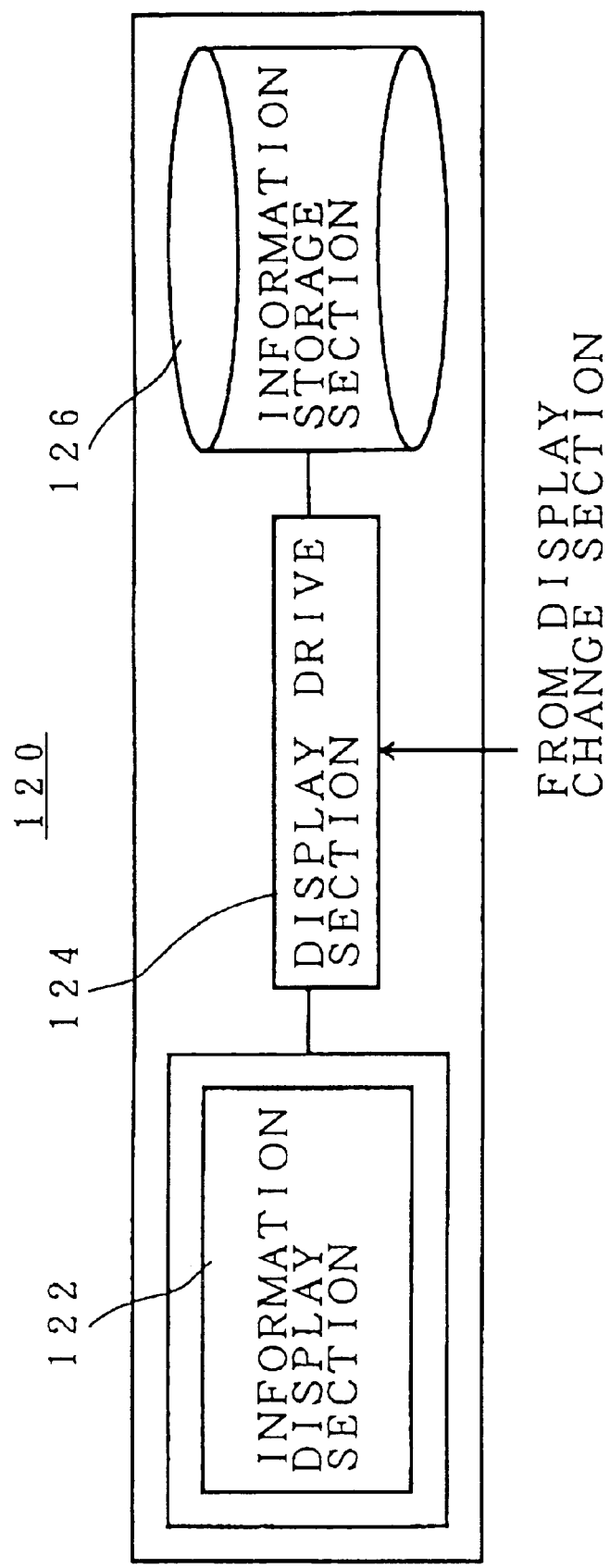
FIG. 17 is a block diagram of an information presentation section 120.

The information presentation section 120 includes an information display section 122 such as a display unit, an information storage section 124, and a display drive section 126 as shown in FIG. 17.

Information as registered in the information storage section 124 such as images, character string or the like is stored in such a manner that each information item makes a pair with its associated display position information. In accordance with the display position information, the display drive section 126 performs displaying of the information display section 122.

Figure 18:
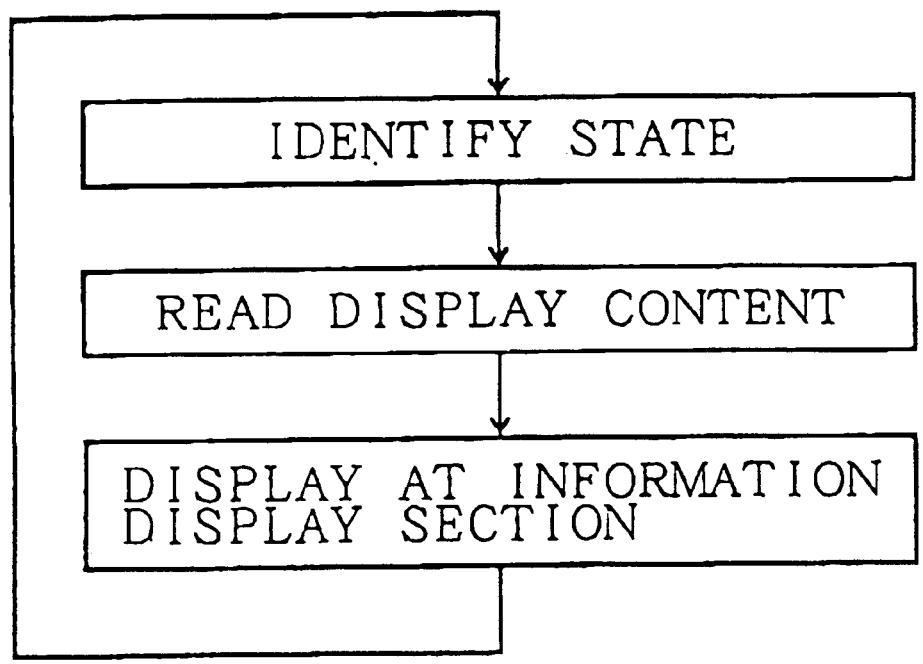
FIG. 18 is a flowchart of the information presentation section 120.

The information storage section 124 and display drive section 126 are implemented using a known general-purpose personal computer(s) pursuant to the flowchart shown in FIG. 18.

The display drive section 126 changes or modifies the display content in response to an instruction from the display change section 150 as will be described later. The term "state" in state identification refers to any states to be identified, including the initial state, several states in the estimation state, resultant determinate state after execution of an intention input, and the like. In each state, information stored in the information storage section 124 is presented.

Figure 19:
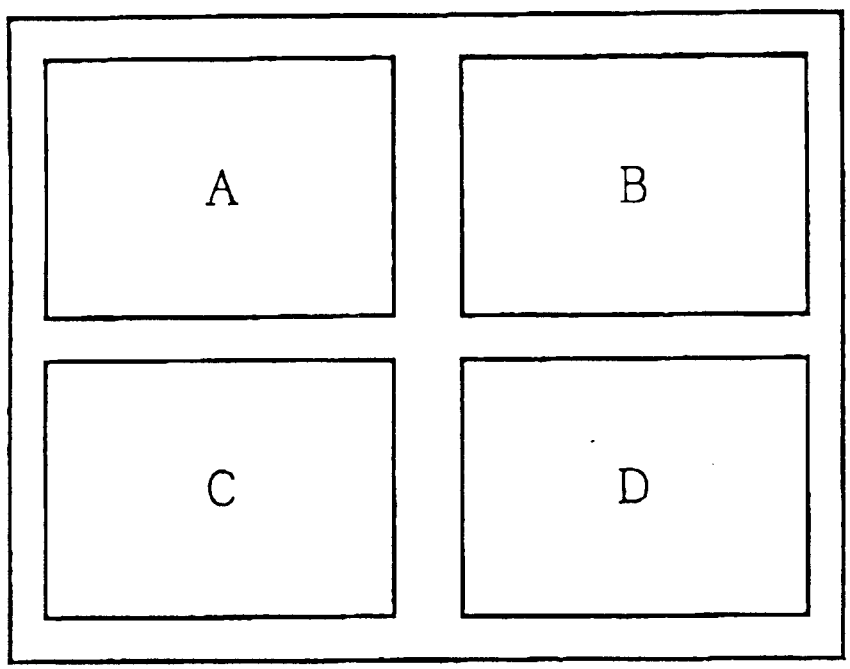
FIG. 19 is a diagram showing one exemplary information presentation.

In cases where the system is an vending machine, commercial products or goods A to D are displayed as shown in FIG. 19.

Information to be selected or the like is displayed in relatively large size in the information presentation section 120. In terms of presentation of information, displaying is carried out in selected size that is determined by taking account of the spatial resolution of the gaze-point detection section 130. In the case of this embodiment, it may correspond to four subdivision of the display screen, which remains sufficiently recognizable even when a gaze detection means comes with low spatial-resolution.

Gaze-Point Detection Section 130

Typically, where the human searches for an object to be selected such as a button or display portion, he or she attempts to look at a corresponding location at which the object being selected is found. The gaze-point detection section 130 is provided for acquiring the direction of such view line and for detecting a specific point to which the view line is being applied, as will be described below (with reference to FIG. 20).

The gaze-point detection section 130 generally consists of an image input section 131, a face-direction detection section 132, a pupil-position detection section 133, a gaze-point determination section 134, and a database section 135.

(Image Input Section 131)

The image input section 131 performs acquisition of color images single-eye a camera. The acquired image is then sent to the face-direction detection section 132.

(Face-Direction Detection Section 132)

An explanation will be given of the face-direction detection section 132 that judges which direction the face is in.

(1) As shown in FIG. 21(*a*), the face-direction detection section 132 executes extraction of the face in images.

This is done by performing region segmentation with respect to the acquired image and finding certain region corresponding to the face based on certain information such as the hue and saturation in respective regions.

Figure 21C:
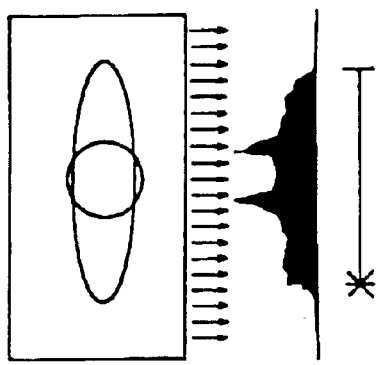
FIGS. 21A–21G are diagrams for explanation of a face direction detecting section 132.
Figure 21B:
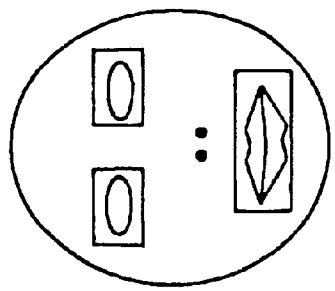
Figure 22:
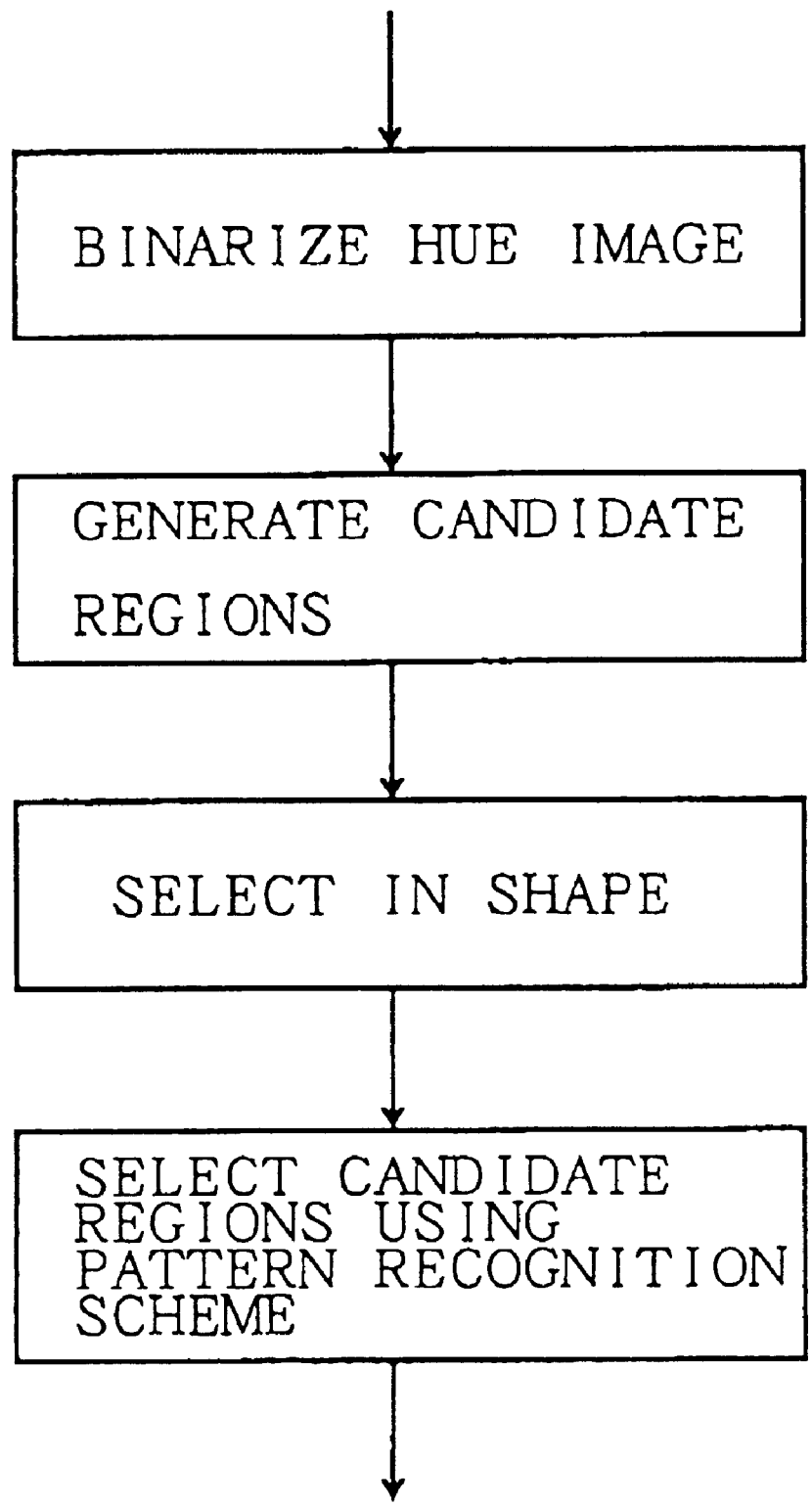
FIG. 22 is a diagram of extraction of face components.

(2) Then, as shown in FIG. 21(b), perform extraction of some elements of faces such as cropping of eye regions and mouth region in accordance with the procedure shown in FIG. 22.

Figure 21A:
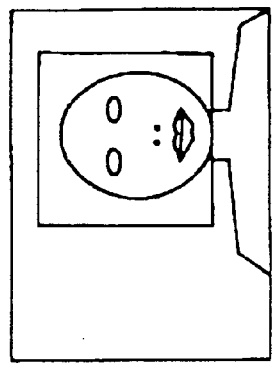

Concerning the face region shown in FIG. 21(a), output certain candidates for the eye and mouth regions which have color attributes different from those of the skin-color regions, by using binarization of a hue image. Next, based on shape constraints, select any regions that are generated by noises such as shadowing and shading. As the characteristic quantity representative of such region shape, perform quantification using a moment invariants, autoregressive model and the like. Furthermore, collate the selected regions with gray-scale patterns such as the eyes and mouth, thus determining eye regions and a mouth region. Here, the collating with the gray-scale patterns is to constitute by KL expansion a dictionary for use in recognition from pre-painted-eye part image and mouth part image, for selecting by complex similarity method or subspace method ones that resemble respective patterns.

(3) After detection of the eyes and the mouth, edge images are then created with respect to the right eye, left eye and mouth as shown in FIG. 21(c). The known schemes such as Sobel filter method and Canny's method may be employed for creation of such edge images.

(4) Then, map the edge image in a direction perpendicular to the one-dimensional (1D) axis direction, performing detection of the inner corner of the eye. Similar processing is applied to the mouth region, detecting the right and left edges of the mouth. Scan the image in a direction normal to the 1D-axis, defining the lowest brightness point as the point of the inner corner of the eye.

Figure 21G:
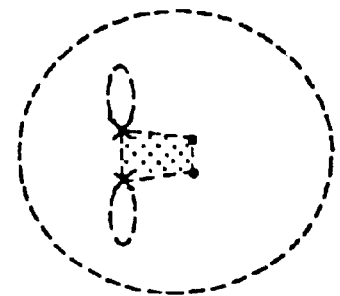
Figure 21F:
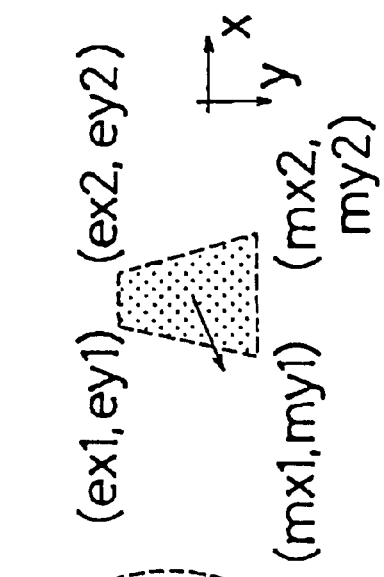
Figure 21E:
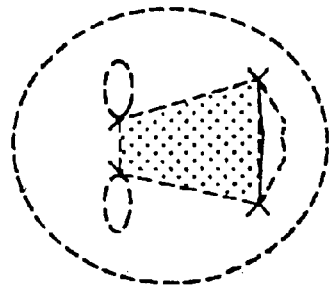
Figure 21D:
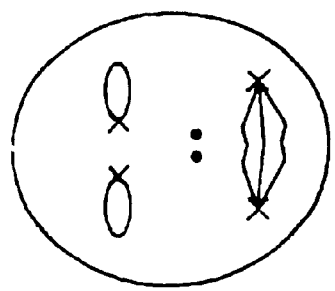

(5) A method is known for calculating the normal direction of the face plane by use of distortion objects based on planar distortion constituted from four points as shown in FIG. 21(e) (A. H. Gee and R. Cipolla: Determining the Gaze of Faces in Images, CUED/F-INFENG/TR-174 (1994)); here, face-plane normal direction is obtained by a database that are created by linear interpolation using the information as to the positional relationship of four points that are experimentally defined in advance and the face-direction information.

For example, with respect to the four positions shown in FIG. 21(f), calculate the horizontal direction parameter. $\alpha$ and vertical direction parameter $\beta$ using the following equations:

$$\alpha = \frac{(mx2 - ex1)}{(mx2 - mx1)}$$

$$\beta = \frac{(my1 - ey1)}{(ex2 - ex1)}$$

It should be noted that calculating the parameters $\alpha$, $\beta$ should not be limited exclusively thereto, and may be done using in a different way—for example, other face characteristics may be used when calculating the face direction.

(Pupil-Position Detection Section 133)

An explanation will be given of the pupil-position detection section 133 which judges where the pupils are in the eyes.

(1) Perform binarization with respect to on the eye's regions obtained in the Lace-direction detection section 132 as shown in FIG. 23(a). Based on the binarization result, find the centroid of black pixels for detection of pupil parts.

(2) Obtain the pupil's centroid, and then define a vector V by using the previously defined tear-duct point (FIG. 23(b)).

(3) Define two straight lines A' and A" wherein line A' passes through inner corner of the two eyes with respect to several points of the tear ducts and mouth edges as obtained by the face-direction detection section 132 whereas line A" connects between two opposite mouth edges. Then, the angular inclinations of these two lines are averaged defining a straight line A (FIG. 23(c)).

(4) Represent as $\theta$ an angle defined between the vector V and straight line A while letting the length of vector V be expressed as $\sigma$. These $\theta$, $\sigma$ are used as the pupil's position parameters.

(Gaze point Determination Section 134)

The gaze-point determination section 134 determines which location is being seen in the information presentation section 120 with respect to the direction of the view line. Calculate a gaze point using the eye position parameters $\theta$, $\sigma$ at the direction parameters $\alpha$, $\beta$ of a given face.

FIG. 24 is a diagram for explanation of the relationship between the face direction (f($\alpha$)) and eye position (g ($\theta$,$\sigma$)) for use in calculating a gaze point relative to the horizontal direction. Here, they are given as:

$$f(a) = d + a$$

$$g(\theta, d) = \frac{d\cos\theta}{(ex2 - ex1)} + b$$

where a, b are certain parameters given in view of difference among individuals or the like. Note that the functions f, q should not be exclusively limited to this, and may be modifiable depending upon the required accuracy, individual differences and the like.

Figure 24A:
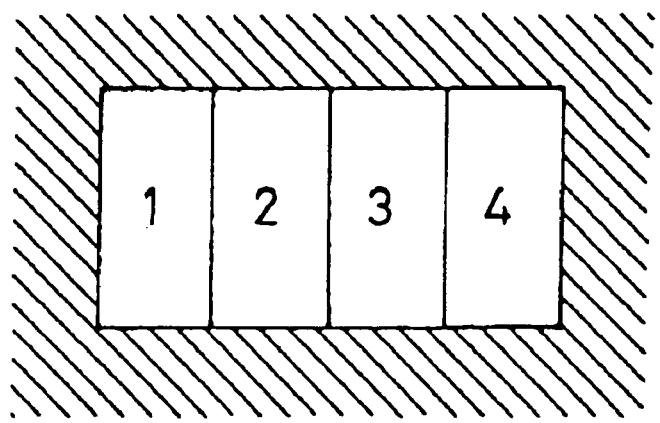
FIGS. 24A and 24B are diagrams for explanation of a gaze-point determination method.
Figure 24B:
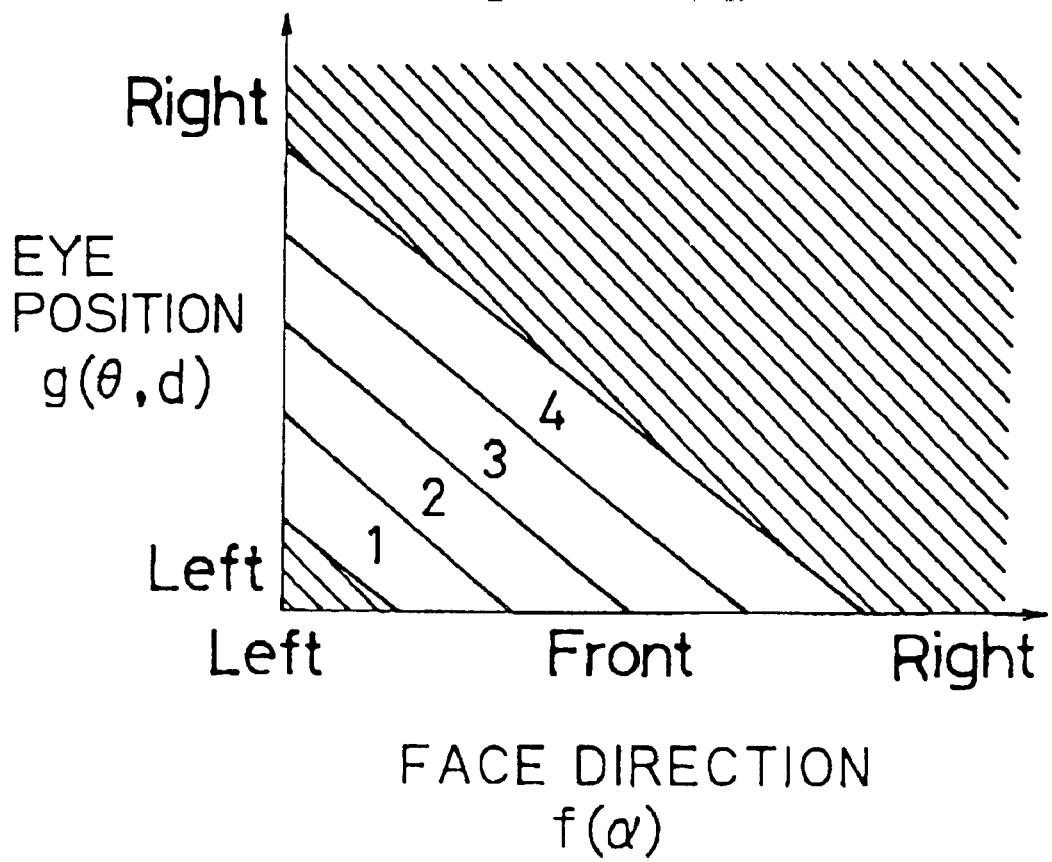

What is shown in FIG. 24(a) is the information presentation section 120, which provides division into four portions in the horizontal direction. At this time, as shown in FIG. 24(b) which indicates the relation of the face direction versus the eye positions, each divided portion constitutes the parameter's subspace when the user is gazing at a corresponding divided one. Qualitatively explaining, it represents the relation which follows: "even where the face looks right, it might look left if the eyes are significantly directed to the left."

The same decision may be done with respect to the vertical direction.

In cases where the person being detected is far from the system, a zoom lens may be used for photographing the person and performing an image processing required.

Figure 37:
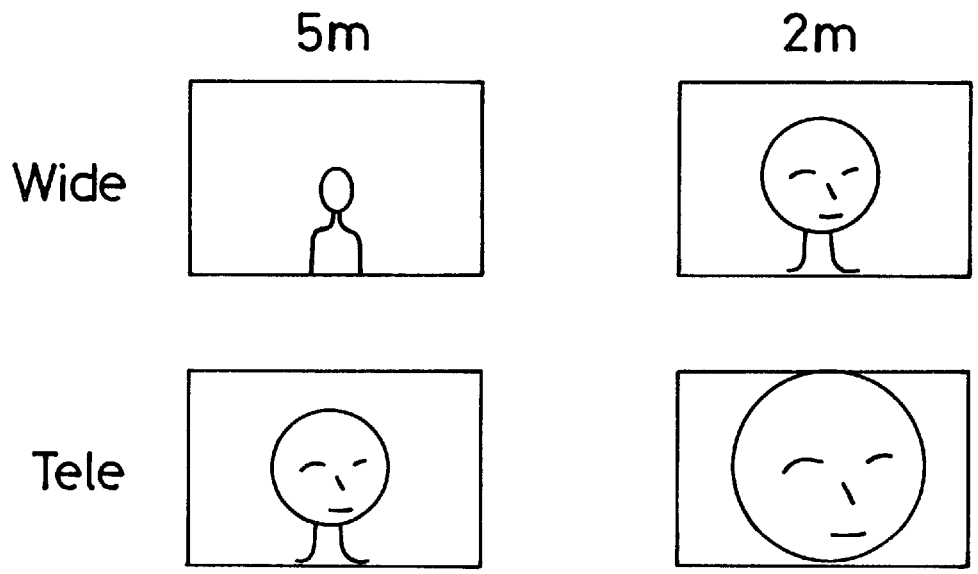
FIG. 37 is a diagram representing photographic conditions of a person to be sensed upon modification of zooming.

FIG. 37 shows several image examples indicating the sizes of a person photographed using a commercially available zoom lens (focal length: 11.5 mm (Wide) to 69 mm (Tele)) under the condition that the distance from the system is changed between 5 m and 2 m.

In view of the foregoing, even when spaced apart by 5 m, it is possible by zooming to attain required resolution high enough to enable identification of elements of faces wherein the gaze is detected using the prescribed algorithm. In the case of 2 m or around it, 11.5 m (Wide) is sufficient; more preferably, dynamically controlling the zooming may enable provision of appropriate size for recognition.

In the case of closer distances, simply prepare the one having a further shorter focal distance.

To find the person to be detected, the zoom lens is set in the "Wide" mode; when a person is coming, the zoom degree Z is suitably adjusted to ensure that the face becomes constant in size. Adjust the zoom degree in such a way that the area S of a face region obtained by the face-detection section and the conversion parameter A as to the zooming degree satisfy Z×S=A (constant).

Additionally, in order to enable dynamic discovery of a target person without having to exclusively use the zoom lens, a camera controllable in panning and tilting may be employed for tracking that person.

(Database Section 135)

The database section 135 includes several kinds of data in accordance with the distance from the system as shown at the lower part of FIG. 24(b), enabling determination of the direction of a gaze point with the face direction weighted when the distance from the system is relatively large.

The gaze-point detection section 130 sends to the prediction section 140 certain information including pairs of data (distance, gaze-point direction) so as to enable determination of gaze-point direction in accordance with the actual distance.

Prediction Section 140

The prediction section 140 performs estimation of information to be selected by the user.

Figure 25:
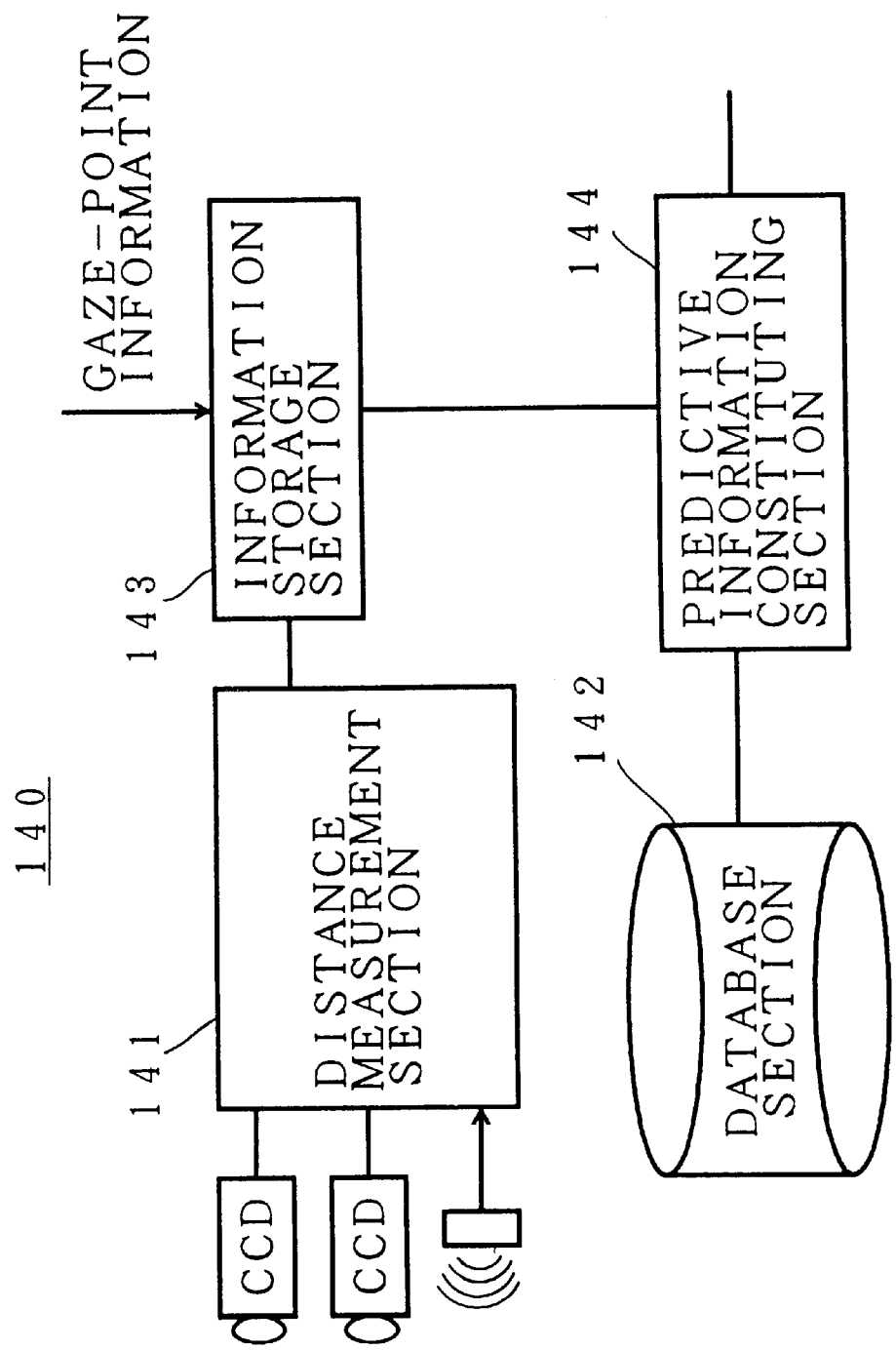
FIG. 25 is a block diagram of a prediction section 140.

The prediction section 140 essentially consists of a distance estimation section 141, database section 142, information recorder section 142, and predictive information constituting section 144 as shown in a block diagram of FIG. 25.

(Distance estimation Section 141)

The distance estimation section 141 calculates the distance between the user and the system. In this embodiment, stereoscopic measurement is carried out obtaining the distance to the user by using triangulation techniques. Note that other measurement schemes may be employed, including ultrasonic sensor-based measurement, a method for defining the distance based on the human's area as captured by a single-eye camera.

Modify the estimation content at respective distances by dividing the distance into three to five regions. In this embodiment, it is divided into three regions defining a system operable range (several tens centimeters), system visual range (several meters), and system ignorance range (farther) in the order of close distance.

(Database Section 142)

The database section 142 has two separate ones: a presentation content database, and action database.

The presentation content database stores therein data with the position information and its content being linked together in the information presentation section 120 as implemented in the system. The position information is represented by a rectangle of (x1, y1)–(x2, y2) whereat each information item is placed while allowing its content and a display form on the information presentation section 120 are represented as a pair.

The action database stores therein some kinds of patterns as to users' action patterns. For example, a variety of patterns which contain action patterns available during operation of the system, action patterns when a user is coming closer to the system, and the like are prepared in advance for use in identifying that the action of the system's user is most similar to which one of such action patterns.

(Information Recorder Section 143)

The information recorder section 143 records therein the gaze directions at fixed intervals.

Each gaze direction is determined by selecting one of those information items fed from the gaze-point detection section 130 in accordance with the distance obtained by the distance estimation section 141, causing its gaze direction to be recorded therein.

The information recorder section 143 is constituted by using a ring-buffer circular queue.

The ring buffer is shown schematically at the lower part of FIG. 27. For example, after completion of storage of information items in the sequence of from 1 to 8, then further storage will be done by replacing 1 with new information. Due to execution of such sequential rewrite, certain "old" information before a fixed time is automatically updated with "new" one. The record contents are registered in the ring buffer with the gaze direction obtained from the gaze-point detection means and the distance information obtained from the distance detection section as well as the acquired time point being as one set of data (gaze direction, acquired time, distance) (see the intermediate part of FIG. 27).

(Predictive Information Constituting Section 144)

The predictive information constituting section 144 operates to estimate in advance what kind of information or what type of product is under request by collating the contents recorded in the information recorder section 143 and the action pattern information stored in the database section 142.

The action pattern information is time-sequential information that may be represented as shown in FIG. 26. Note that the gaze point in the drawing is represented one-dimensionally for purposes of explanation, although it is practically the 2D movement of a view point.

FIG. 26(b-1) represents "coming closer while gazing at certain point."

FIG. 26(b-2) represents "looking at a fixed point while coming closer up to certain position, and further approaching while directing toward the system."

FIG. 26(b-3) represents "coming closer while looking around restlessly."

FIG. 26(c) represents "looking around restlessly at distant locations."

Several action patterns including the above ones are prepared in advance and registered in the database section 142.

The estimation method changes its function by taking account of the distance to users.

[System Operable Range]

The action patterns within the system operable range may involve (a-1) "continuing looking at interesting ones," (a-2) "coming closer to look at interesting ones," (a-3) "wanting other information in the absence of any interesting ones," (a-4) "having no interests," and the like.

In the cases of (a-1) "continuing looking at interesting ones" and (a-2) "coming closer to look at interesting ones," gaze-point information as to which information is being selected is sent to the result output section 170.

Where information with no interest or concern is under presentation, when the gaze point is directed to the outside of the information presentation section 120, it is determined that no interest is shown as in the case of action pattern (a-3) judging that new information is necessary. This will be described later in connection with the function of the display change section 150.

[System Visual Range]

In the system's visual range, the user is capable of looking at not only the system but also other information presentation objects. For example, imagine that he or she wants to get a ticket of super-bullet trains on Shinkansen line at an automatic ticket selling machine. In this case, the route guidance chart or the like is typically presented at the upper portion of an array of ticket machines, allowing travellers to look at the chart and affirm the destination and its corresponding fee or charge. At this time, if specific information can be acquired which indicates that a target person looks at which part of the route guidance chart, it will enable rapid selection of his or her desired ticket by presenting some price tables possibly corresponding to an appropriate route section as desired by the traveller while eliminating displaying of the other unnecessary sections.

This situation will be considered as the case of the action pattern (b-1) shown in FIG. 26. At this time, what kind of information is presented may be determined based on the fact that the traveller have looked at what kind of information. For instance, in the foregoing example, there is employed a method for presenting some possible candidates concerning destination depending upon the fact that s/he looked at which side—the east or the west—of the route guidance chart. Under this condition, if the information in the ring-buffer is as shown in the middle part of FIG. 27, then determine the contents of information to be presented based on the information at a gaze point (x1, y1) at which s/he looked in the distance. Presenting estimated information in this way may result in a decrease in the overall operation time.

[System Ignorance Range]

In the system ignorance range, when it matches the action pattern shown in FIG. 26(c), the initial state remains without execution of any estimation.

In the case where the action patterns are the 1D-wave patterns as explained previously in connection with respective drawings, the identification method thereof is to select as its action pattern the one having the maximum similarity with a square-sum of difference being as an indicator of similarity at every time point of the registered and input patterns. The identification method may alternatively be the prior known pattern recognition scheme using simple similarity or complex similarity, DP matching, neural networks or the like, if appropriate. When no action patterns are matched, or when the processing fails, re-start to serve for the human in the preset initial state.

When the instruction content is changed in response to an instruction from the prediction section 140, the following two courses are available: displaying the position of a gaze, or modifying the display content of information to be selected. The prediction section 140 supplies the display change section 150 with an instruction(s) as to the gaze position and estimated content. When the presentation content is to be modified, instruct the information presentation section 120 to change or modify the state. In responding to this, the information presentation section 120 performs state identification for presentation of information, based on resultant information supplied from the prediction section 140.

Also, supply the result output section 170 with the estimated action pattern and the selection content at each time point. At this time, it is unlikely that only one selection information item is send exclusively; on the contrary, all the selection contents during an access to the system for making a selection are sent together to the result output section 170. Determining one from the plurality of contents sent thereto is done in such a way that the one the user looked at on certain time designated by the result output section 170 is specified as the selection content.

Display Chance Section 150

Figure 28:
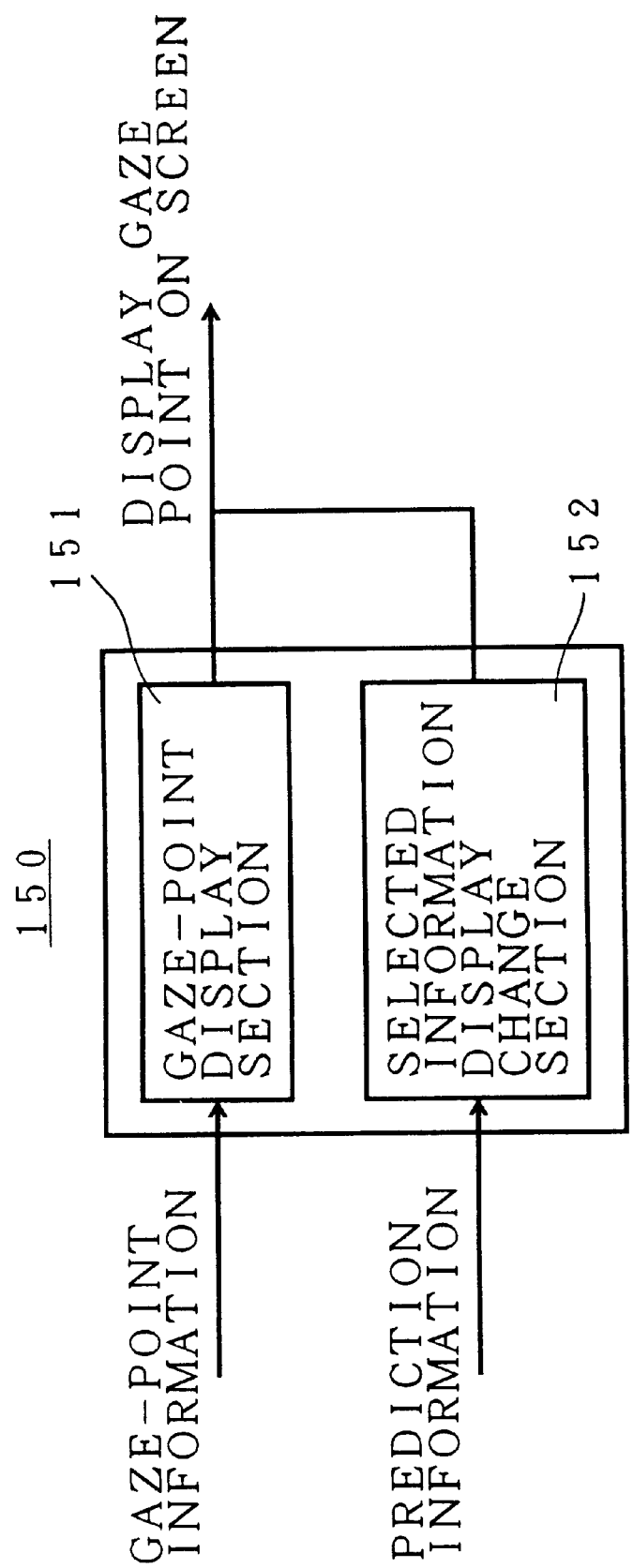
FIG. 28 is a block diagram of a display change section 150.

The display change section 150 essentially consists of a gaze-point display section 151 and a selection information display change section 152 as shown in FIG. 28.

(Gaze-point Display Section 151)

Figure 29A:
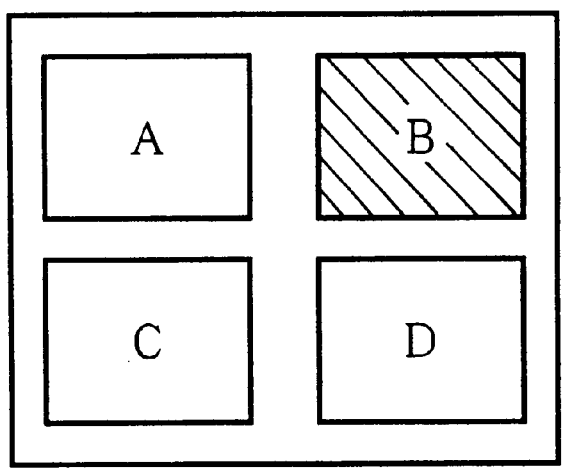
FIGS. 29A–29C are diagrams showing an exemplary display change in the information presentation section 120.
Figure 29B:
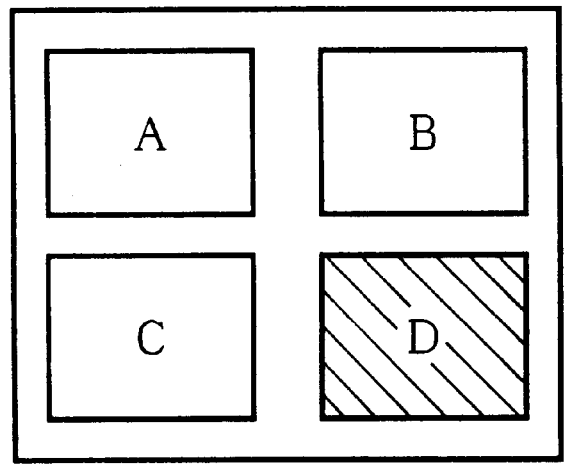
Figure 29C:
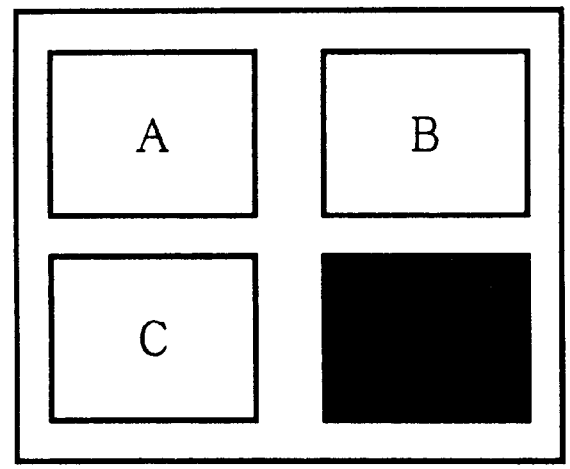

The gaze-point display section 151 operates to display specific information portion that is at the position of a gaze-point sent from the prediction section 140 while changing its color attribute, for example. Alternatively, it changes the display by using reversal indication or the like to enable the user himself to be aware of which information is being steadily looked presently. For instance, like the case (a) of looking at a product B, or looking at a product D as shown in FIG. 29, a steadily looked portion is reversed for output. The display is changed as shown in the case (c) where selection is made final.

(Selection Information Display Change Section 152)

The selection information display change section 152 changes or modifies the presentation contents in response to instructions sent from the prediction section 140. Where the user's gaze point is out of the information presentation section 120, the display information is scrolled in that direction accordingly in a way as will be described below.

Figure 30:
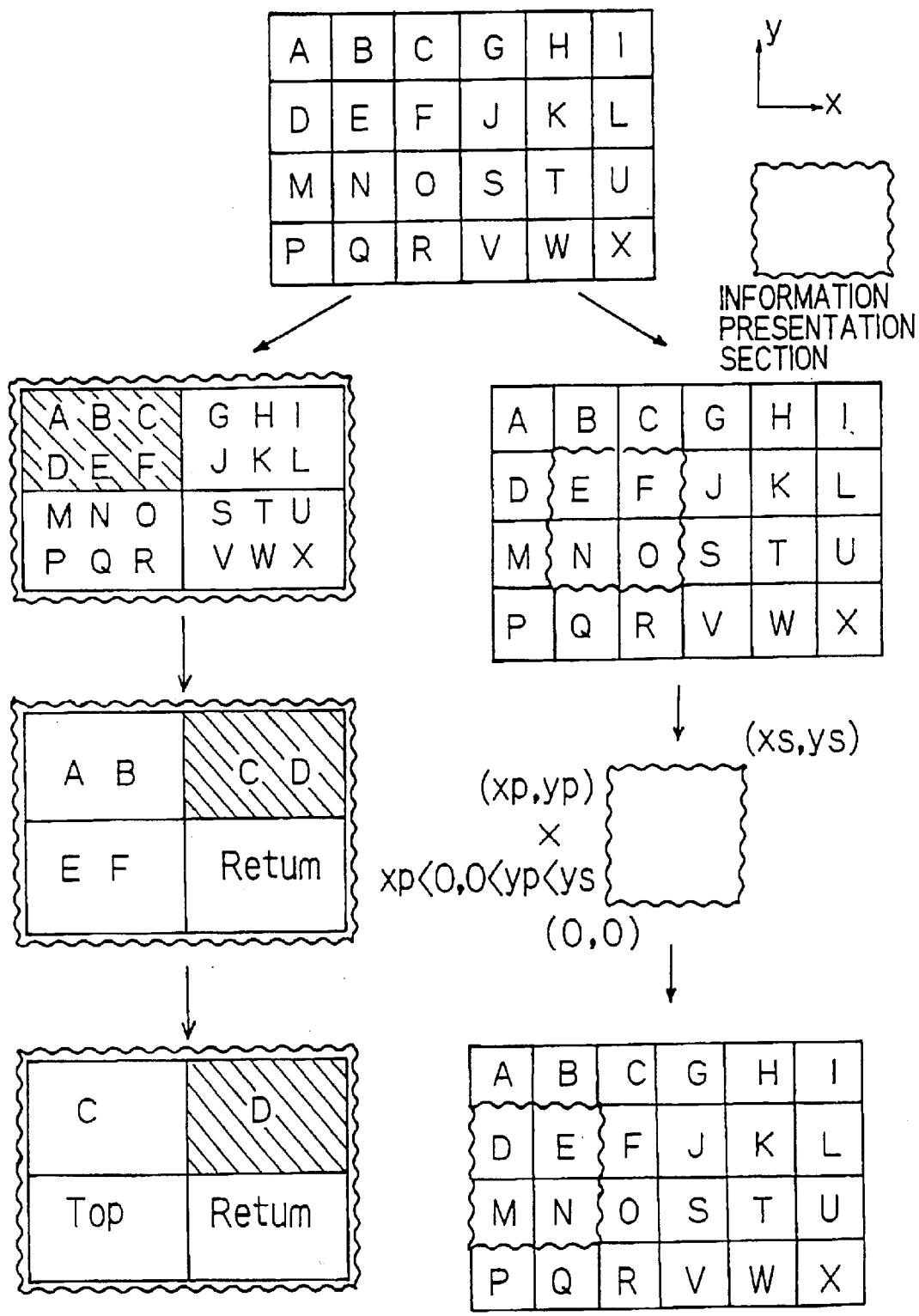
FIG. 30 is a diagram showing one exemplary scroll function in the display information change example.

Generally, where the displayable information items are less in number, for example, where only four different information items remain displayable as shown in FIG. 19, it will possibly happen that 24 different information items are under selection as shown in FIG. 30. If this is the case, hierarchical selection is typically carried out. As shown in the left-hand column of FIG. 30, first make a selection in the general classification at the upper-left location; then, make another selection in the middle classification at the middle-left location; finally, select a target object (here, D is selected) in a hierarchical sequence. However, in view of the fact that the advantages of using a gaze lie in the capability of showing an intention such as "looking at nothing in the absence of any information displayed" as well as the possibility of looking at any possible direction in which some target information is available. Thus, an information display method shown at the right-hand column in FIG. 30 is possible.

The right-hand section of FIG. 30 shows four information items boxed in bold lines being presently displayed by the information presentation section 120. Here, look at the location including a target information item (D, for example). More specifically, as indicated at the middle right portion of the drawing, the displayed location is changed by looking at a marking "x" that is located outside the information presentation section 120, permitting modification of the information presentation as shown at the lower right portion.

Figure 32:
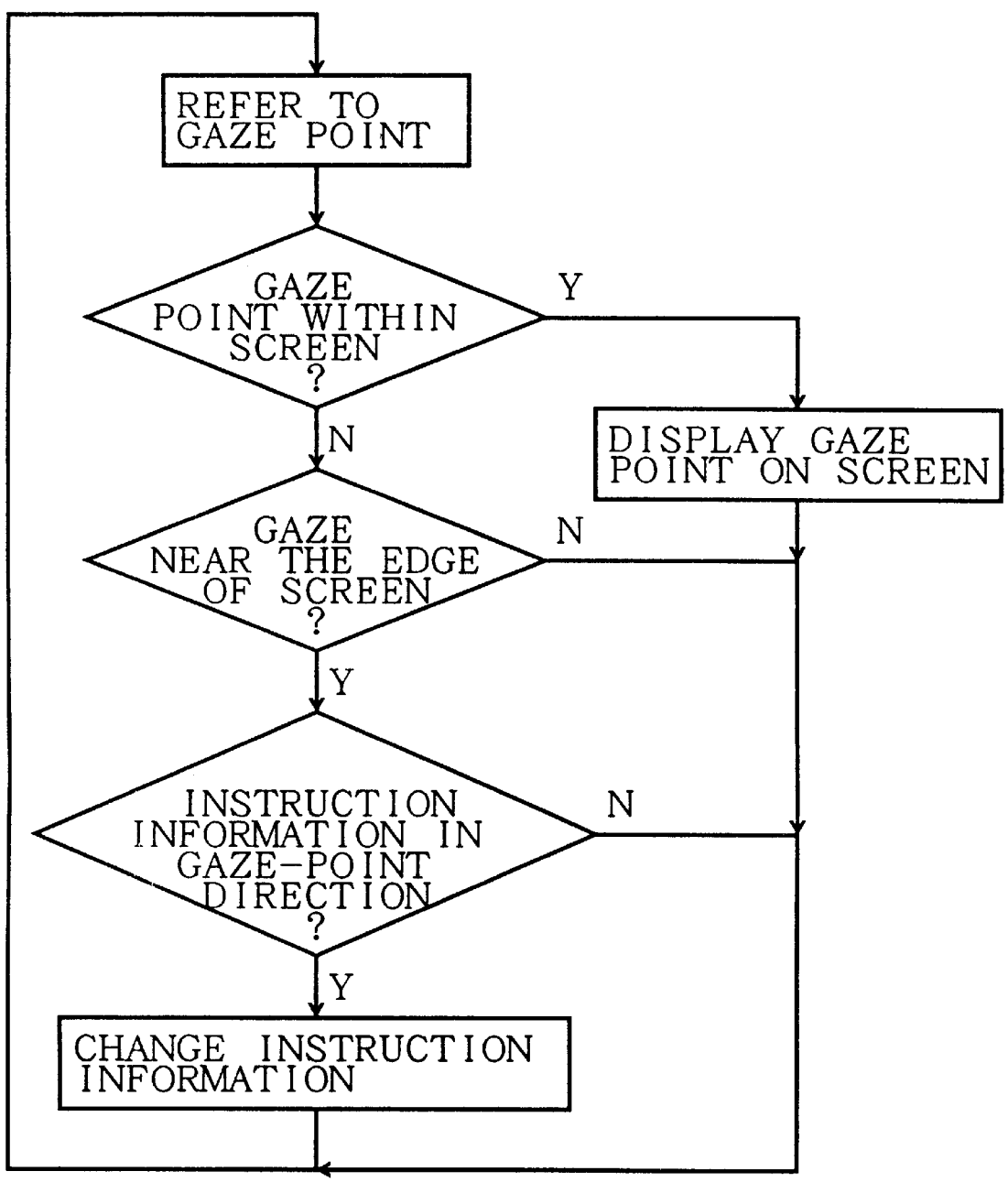
FIG. 32 is a diagram of exemplary operation of a selected-information display change section 152.

For the coordinate system (x, y) in FIG. 30, represent the range of screen as (0, 0)–(xs, ys). Consider that the gaze point (xp, yp) is out of the range (0, 0)–(xs, ys). In this case, if information is present in a corresponding direction as the content of presentation information, then change the presentation information. A flowchart of this is shown in FIG. 32.

At this time, the user's gaze point is actually out of the information presentation section 120; however, the user can visually verify by away-from-view-point looking whether the presented information is changed or not. Where the display is changed or modified, displaying of the gaze point is again performed when the user's gaze is directed at the inside of the information presentation section 120.

Figure 31:
FIG. 31 is a diagram showing one exemplary resolution conversion in the display information change example.

In the case of employing a gaze detection apparatus with low accuracy, when the user looks at a miniaturized display object, the following function may be used to change the display resolution. Consider the case where fine and miniaturized patterns are being displayed as shown in the upper section of FIG. 31. When the user continues gazing at an ellipse-like section shown in the drawing, its corresponding display content is enlargedly displayed on the information presentation section 120 with its resolution being changed as shown at the center part of FIG. 31. For display information items finer (smaller) than a predefined size, necessary display information therefor has been stored for use in displaying the same in an increased size. Furthermore, it is also possible to change the size hierarchically as shown at the lower part of FIG. 31. By changing the display resolution using the gaze information in this way, it becomes possible to increase the selectivity during presentation of information.

Intention Transmission Section 160

Figure 33:
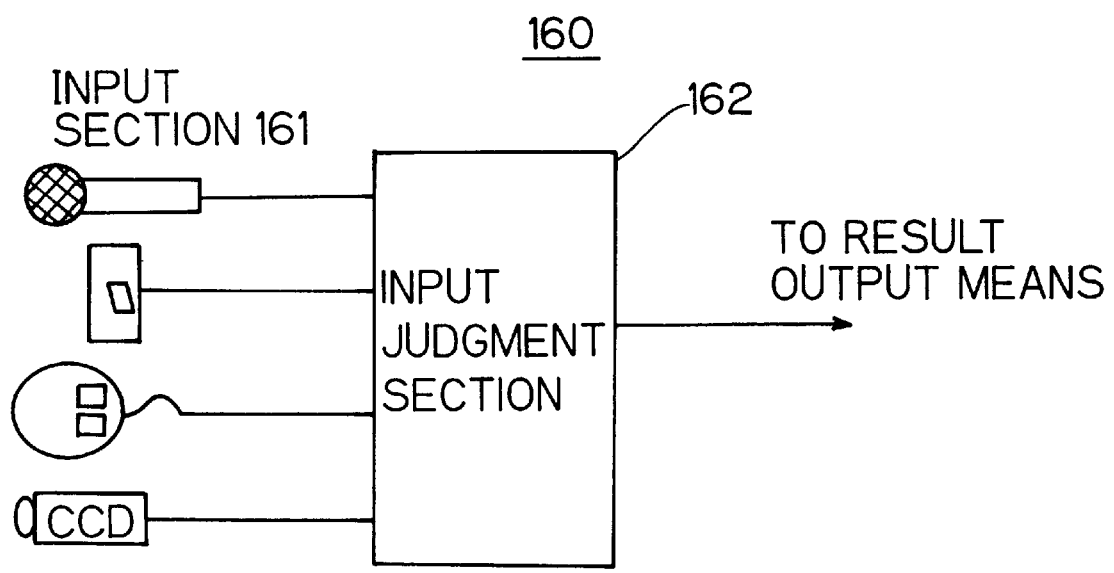
FIG. 33 is a block diagram of an intention transmission section 160.

The intention transmission section 160 generally consists of an input section 161 for input of voice signals, switch changeover signals and the like, and an input judgment section 162 which recognizes the contents of input signals (see FIG. 33).

The input section 161 includes a microphone, switch, mouse device, camera or the like, which supplies its input result to the input judgment section 162. The input judgment section 162 analyzes the input contents by taking account of the type of input device and content thereof, and passes the input information to the result output section 170.

As the input judgment section 162 in the case of employing a voice input device, a speech recognition apparatus is employed for the input judgment section 162. For example, when the user makes a speech such as "take it to me" while looking at certain product, such speech is input through the input device to the speech recognition apparatus, which generates and supplies a recognition result to the result output section 170.

By outputting information at the user's gaze point simultaneously when the input information is entered, specific information at a gaze location will be selected accordingly. For example, by saying a simple phrase or word such as "take it to me" or "this" while gazing at the user's preferred information, it is possible to select corresponding information at the gaze point immediately when the word or phrase is spoken.

Other input methods are available: In the embodiment of the vending machine, the input device 161 may be attached to the coin/bill entrance port thereof letting charging of money be used as an input signal.

Result Output Section 170

Figure 35:
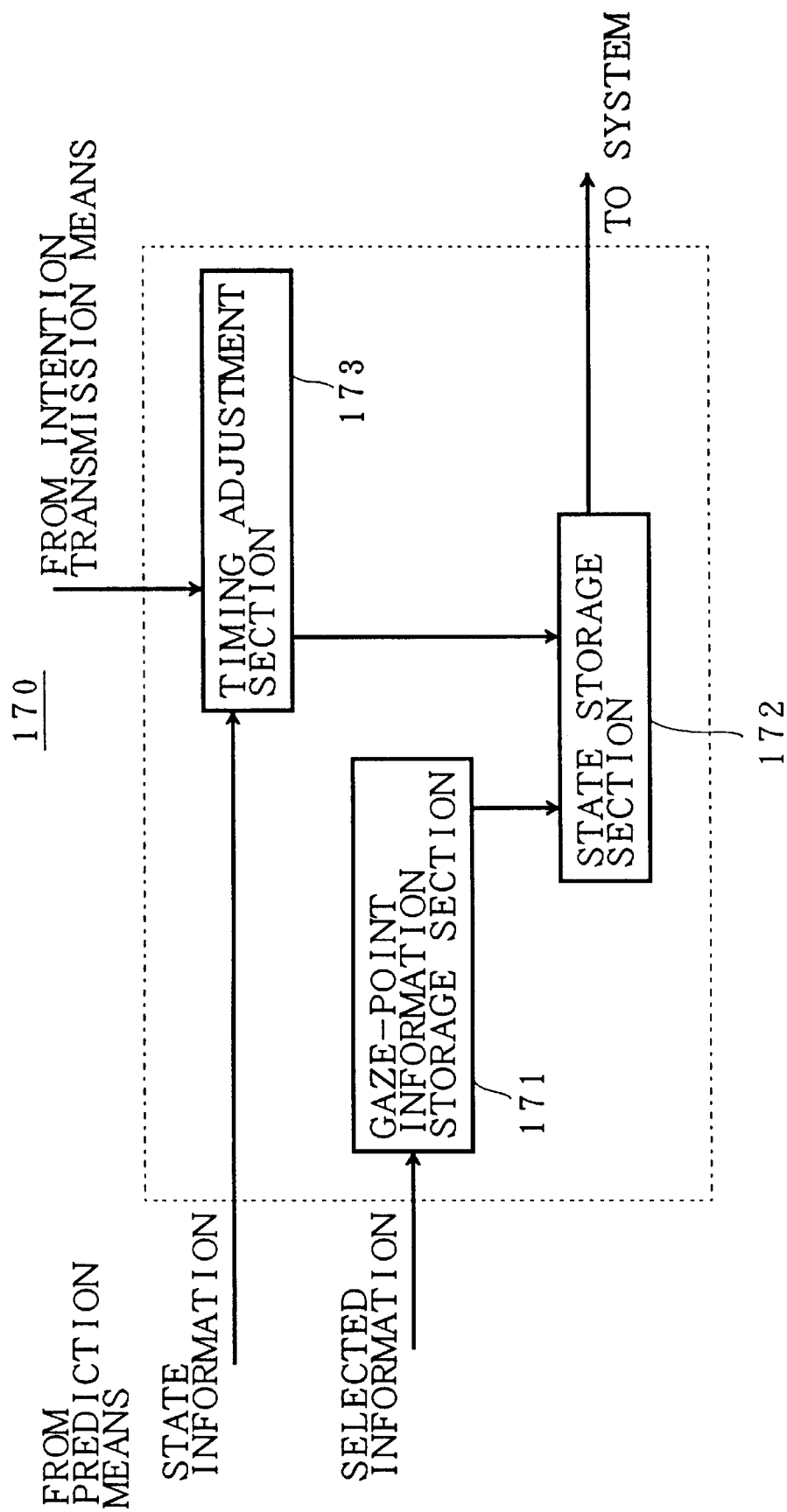
FIG. 35 is a block diagram of a result output section 170.
Figure 36:
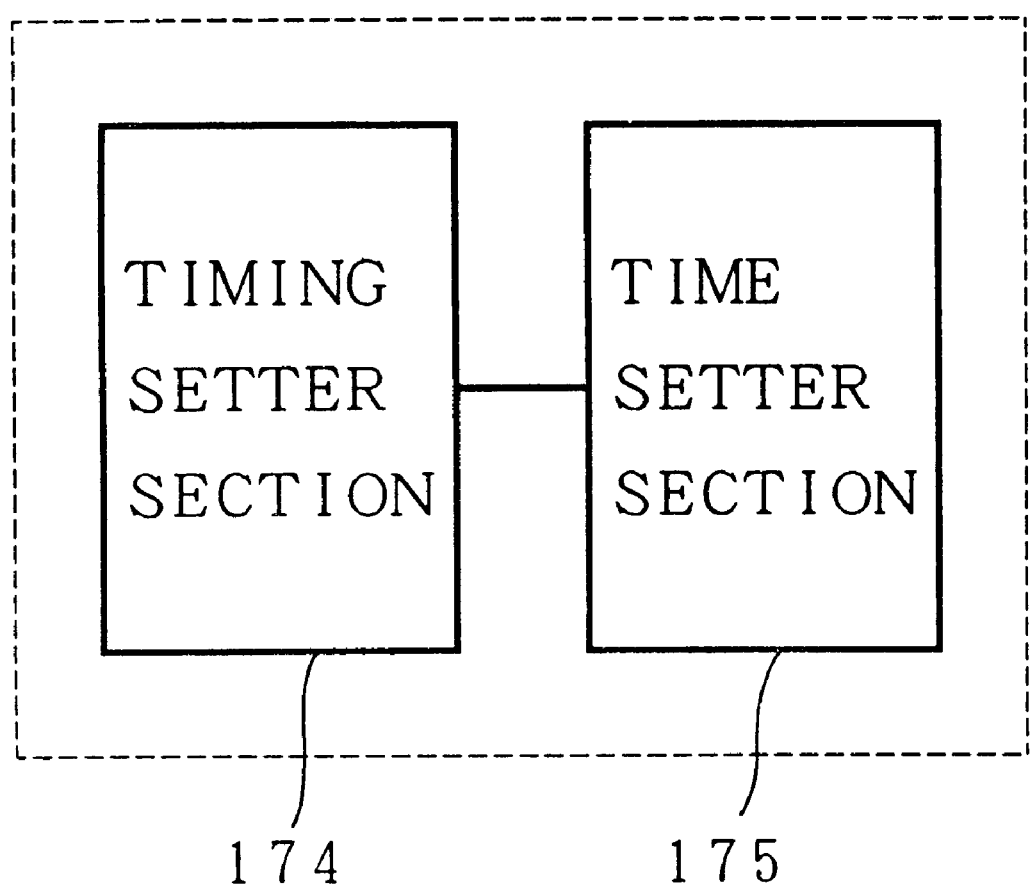
FIG. 36 is a block diagram of the timing adjustment section 173.

The result output section 170 includes a gaze-point information storage section 171, a state storage section 172, and a timing adjustment section 173 as shown in FIG. 35.

(Gaze-point Information Storage Section 171)

The gaze-point information storage section 171 stores therein what is the user's gazing information or product. It also stores any information estimated by the estimation section 170.

(Timing Adjustment Section 173)

The timing adjustment section 173 performs adjustment of the "simultaneousness" of a time point at which the user selected one from several objects being presented by use of his or her gaze versus a time point whereat an input is made by the input section 161. It sets when and which information item the user is gazing at is to be output upon receipt of input information. The timing adjustment section 173 is a means for determining an intention-transmission time point by evaluating the input time point of one or a plurality of input sections 161, which means includes a timing setter section 174 and a time setter section 175.

Figure 34:
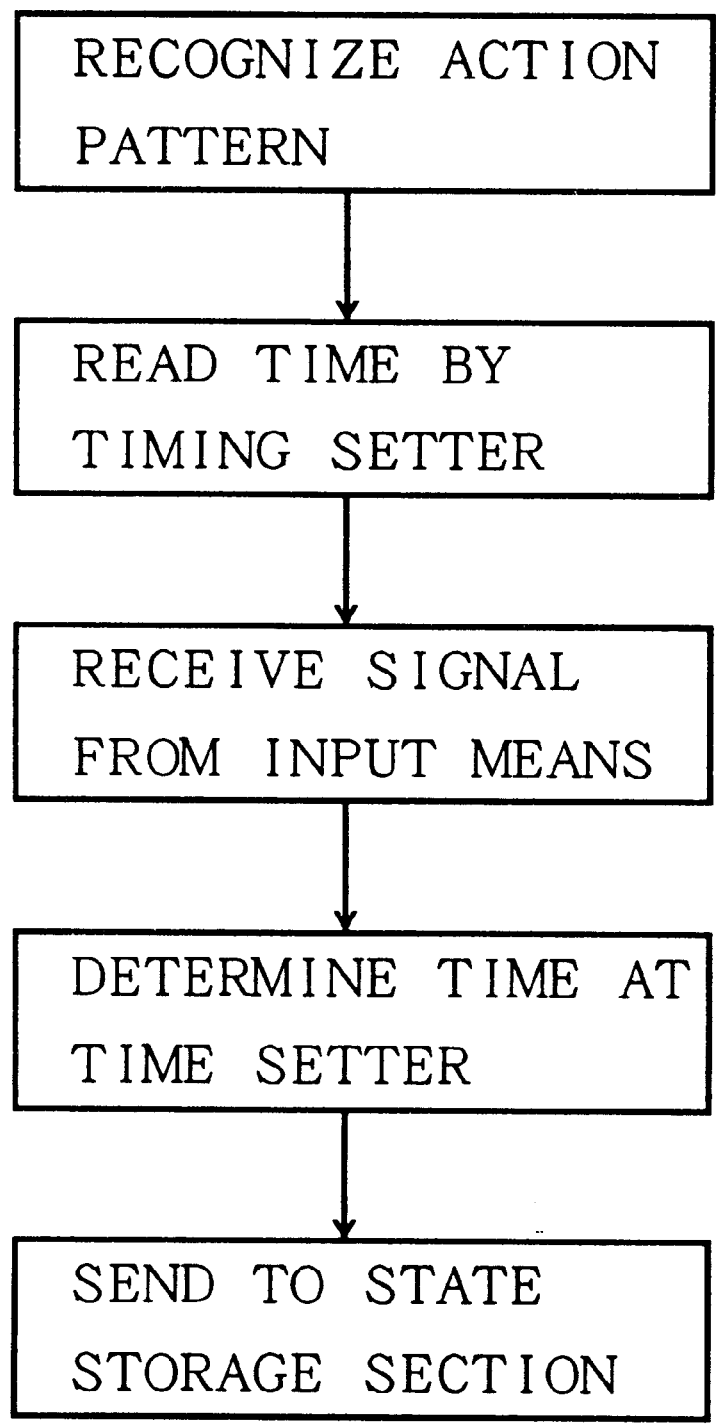
FIG. 34 is a flowchart of a timing adjustment section 173.

An operation of the timing adjustment section 173 is shown in FIG. 34.

In the timing setter section 174, the timing data with respect to each action pattern has been obtained experimentally, for providing appropriate timing that maximizes usability. The time setter section 175 sends to the result output section 170 the total-sum time point which is the sum of a time point preset by the timing setter section 174 and a time at which a signal is supplied from the input judgment section 162.

For example, assuming that the time preset by the timing setter section 174 is $t_k=0$, when the user is in the (a-1) "continuous gaze" pattern, then send to the state storage section 172 a specific time point tin input from the input judgment section 162.

Another input example will be described which is drawn to the embodiment using the vending machine, wherein the input device 161 is attached to the coin/bill entrance port thereof letting charging of money be used as an input signal. In this case the input judgment section 162 attempts to determine the amount of money charged. The timing setter means selects a corresponding product for sale at which the user's gaze point is applied during a time period after the timing-set time $t_k$ has elapsed since the time point t1 when the money was charged. Setting $t_k$ as $-1.0$ (sec)$\leq t_k \leq 1.0$ (sec), any desired product is selected by "charging a coin(s) while looking at the product" without the need of depressing buttons. In this case, it can frequently occur that the user puts his or her gaze on or near the coin/bill entrance port when charging a required amount of money. Accordingly, selection of a product can be achieved by setting the timing-set time $t_k$ at a time point after elapse of several seconds and by continuing gazing at the preferred product to be selected for a while after completion of charging the required money.

(State Storage Section 172)

The state storage section 172 outputs the initial state and estimated state as well as final selected state, stores therein these states and corresponding gaze-point information in the states, and sends the same to the system or other means. If in the final selected state, the system receives from the result output section 170 information or product at the user's gaze point or the like, and then performs initiation of selling, servicing or the like. Other operations such as displaying of such information may be performed.

Several modifications will be described below.

Modification of Information Presentation Section 120

The information presentation section 120 should not be limited only to those which dynamically change in a way as in display devices. For example, it may be arranged such that a stationary panel for constantly indicating products and information items is arranged at or near the apparatus.

In cases where the stationary information presentation is made rather than dynamically displaying of the same on the display screen, illuminant members such as lamps, LEDs or the like may be employed so as to facilitate recognition of the direction of a gaze point.

Modification of Gaze-Point Detection Section 130

Although the non-contact gaze detection scheme is employed using a single-eye camera in the foregoing embodiments, the gaze detection should not be exclusively limited thereto, without regard to contact or non-contact type.

For example, there may be employed a method for image-capturing a target person using a plurality of cameras and for defining the face and eye directions, as has been disclosed in a paper (Akira Tomono, Fumio Kishino, Sachio Kobayashi, "Attempt of Pupil Extraction and Gaze Detector Permitting Head Movements," Transaction of Institute of Electronics and Communication Engineers of Japan (D) Vol. J76-D-II, No. 3, pp. 636–646 (1993)).

Other than the machines or apparatus aiming at rapid operations like the example of vending machine, it will possibly happen that accurate gaze detection is required in certain applications that handle a large amount of data for identification, for example. In such cases, contact type gaze detection schemes may be employed-such as an eye-camera, eye-trackers or the like.

Modification of Intention Transmission Section 160

The intention transmission section 160 may employ a means for attaching buttons or equivalents thereof to the system, other than the aforesaid voice input method and the coin/bill charge input method as shown in the above embodiment; in addition, while detecting the face direction, the intention transmission section 160 may use a transmission scheme which follows. Perform an action such as moving the neck upward and downward ("nodding" action). As described above, a means for detecting an action based on the image information may be added in the alternative of inputting.

Additionally, where the intention transmission section 160 has a highly advanced input judgment section such as speech recognition or the like, this may be modified in configuration such that it offers extra operations to distinctly change the display content in response to the content of its input. Practically, the display change section 150 provides presentation of different information when the user orally inputs by saying "Next content."

The mouth detection means may be replaced with a nose detection means for detecting the nose in images. One possible arrangement of this nose detection means is as follows. When generating the eyes and mouth candidates by binarization of a hue image, specific portions have been found which are different in color from the skin portions; accordingly, two nose holes or nostrils may be detected simultaneously by performing—with respect to each portion—a pattern identification with a dictionary as provided using partial nostril images which has been photographed to contain the two nostrils.

And, in the case of detecting the face direction, a specific plane may be defined which connects two inner corners of the eyes and two nostrils together (see FIG. 21(g)).

Modification of Display Change Section 150

The gaze-point display section 151 may be arranged so as to directly display the gaze point using a cursor or the like other than the color-conversion/reversal displaying of information.

Alternatively, the gaze-point display section 151 per se may be removed away. In other words, the purpose is to enable the human to be constantly aware of how the gaze point is changing; on the other hand, certain applications can arise that require prohibition of such acknowledgement. In this case the intention transmission section 160 may be modified in arrangement so as to enable the user to become aware of the gaze-point position only when designated.

In the selection information display change section 152, it may be combined with the intention transmission section 160 so that scrolling of information is effected only when an intention is transferred—for example, when a signal of "change the display" is supplied thereto.

Alternatively, the display change section 150 may be deleted from the system; still alternatively, a method may be employed which performs prediction and selection based on certain stationary or fixed display content.

Fourth Embodiment

A fourth embodiment will be explained. This embodiment is arranged to change over the device for detection of a gaze point in accordance with the distance between the user and the system.

For instance, when the distance ranges from 2 to 5 m, use the previously mentioned gaze-point estimation section 130; when the distance ranges from 30 cm to 2 m, use the gaze detection apparatus 50.

Figure 38:
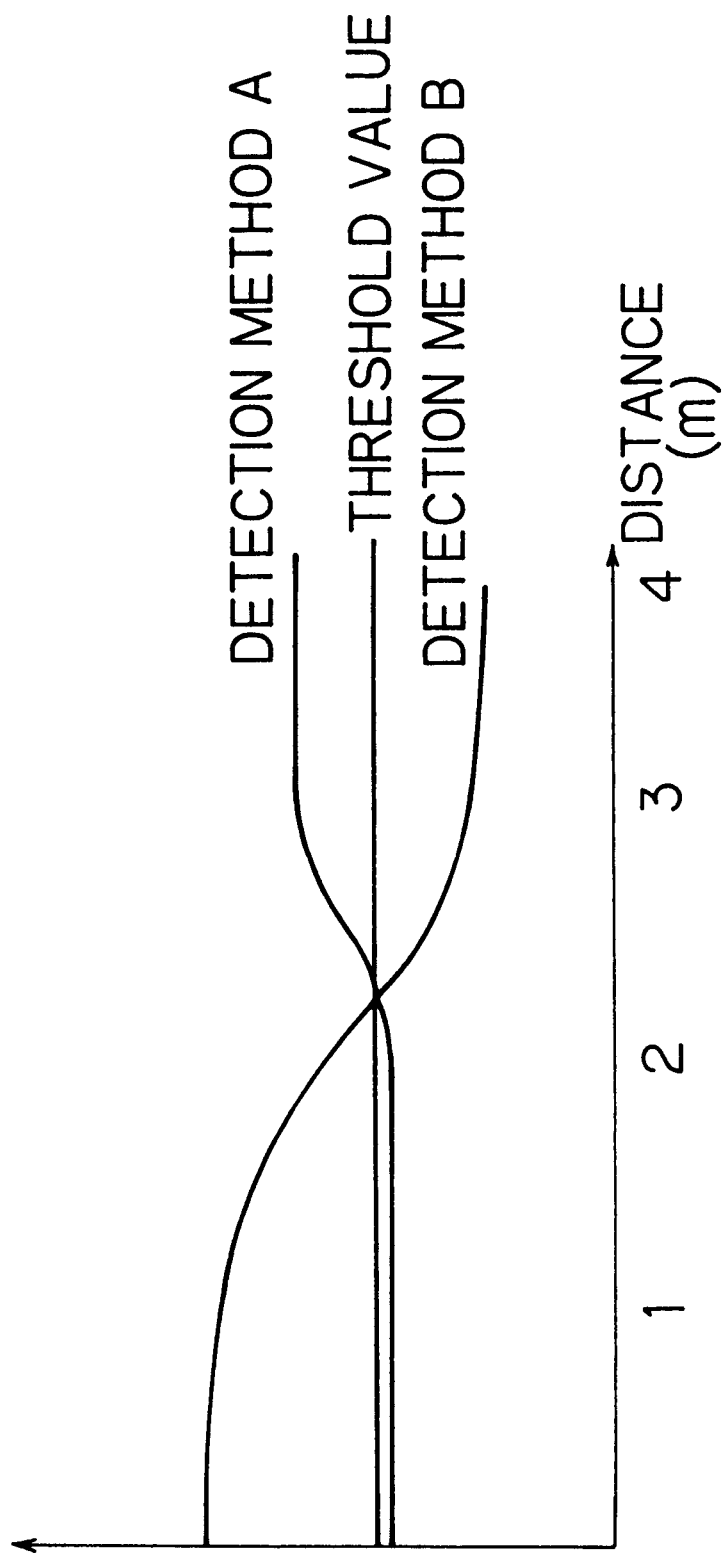
FIG. 38 is a graph representing the gaze detection accuracy.

The reason for adaptably changing between these devices is to retain the detection accuracy under situations that each device may vary in detection accuracy with a change in distance as shown in FIG. 38.

The reference for such changeover is determined by defining the distance L to a target person obtained by the distance estimation section 141, comparing the distance L with pre-measured detection accuracy data of each detection device, and utilizing an output result of one device having the detection accuracy greater than a preset threshold value thereof when it is at respective distances.

In FIG. 38, the gaze detection apparatus 50 is employed in a coverage up to 2 m whereas the gaze-point estimation section 130 is used in the remaining range.

Note that more than two gaze-point detecting devices may be employed together.

Note also that the changeover device that directly makes use of the distance information as mentioned above is irrelevant to the action pattern database. However, it may alternatively be arranged such that in the place of performing changeover directly based on the distance information, gaze-point detecting devices are changed using specific information which has been prestored in the action database to describe when a change is effected with respect to which one of gaze-point detecting devices.

Fifth Embodiment

Figure 39:
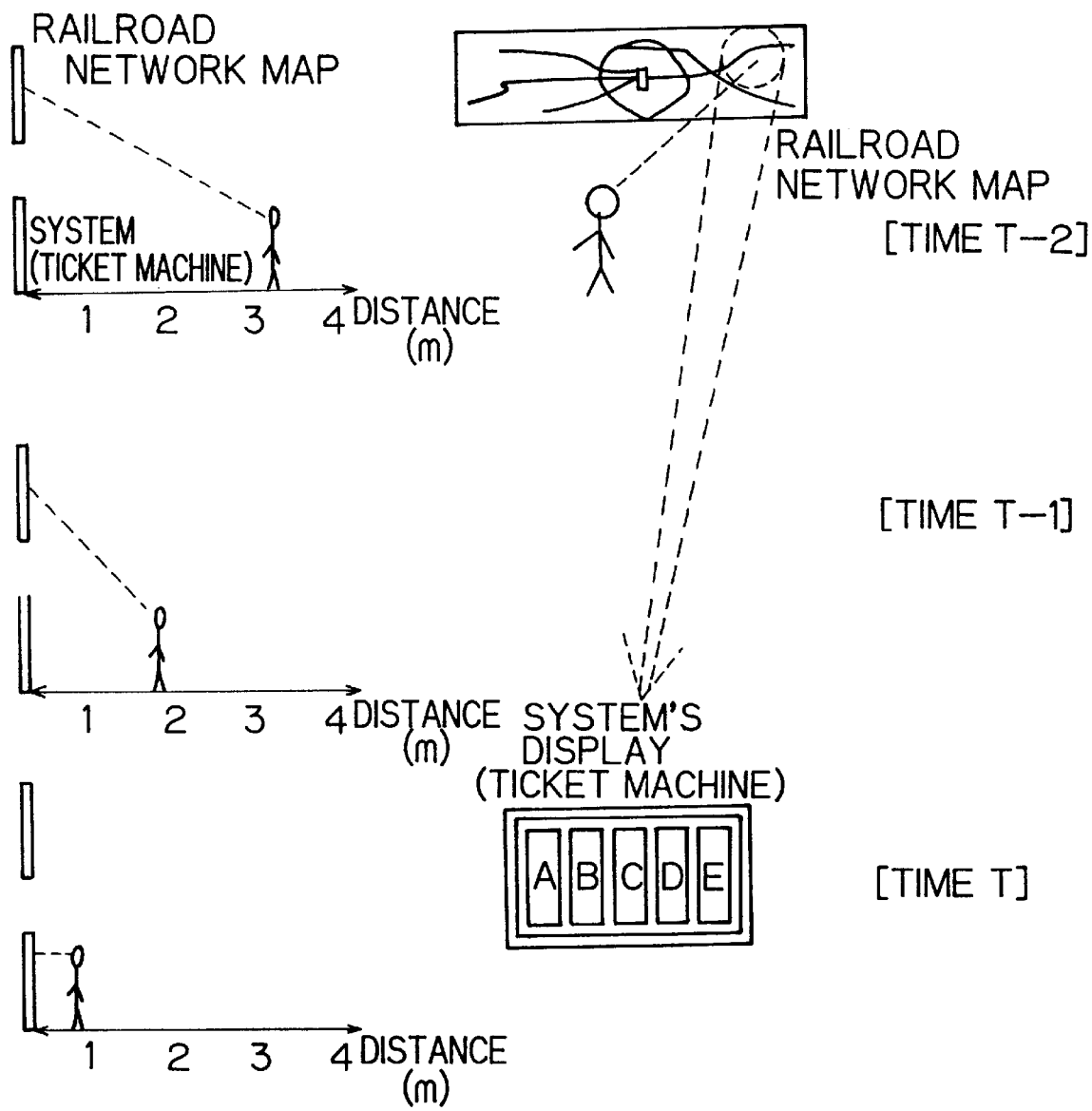
FIG. 39 is a diagram for explanation of a changeover between the distance-dependent prediction and the gaze-point detection.

A fifth embodiment will be explained. In the following description of this embodiment, there will be explained practically with reference to FIG. 39 the case where a changeover between the gaze-point detecting devices is performed in accordance with the user-to-system distance.

As has been described in connection with the example using the automatic ticket selling machine in the section of the predictive information constituting section 144, the user looks at the railroad network map in the distance at the time point T-2. In such case, the gaze detection is carried out in such a way that the gaze-point estimation section 130 is used to detect the face direction of the user at a location far from the system for estimation of the direction of his or her gaze. In this case, a judgment is made to determine that the person is within the "system visual range," then select a corresponding pattern from the previously registered action patterns.

In the case of an action pattern indicating that the user is coming closer to the system while looking at the railroad network map, the device for detecting a gaze point is changed, at a time T-1, from the gaze-point estimation section 130 to the gaze detection apparatus 50. At this time, the gaze detection is being performed at each apparatus independently allowing the system to selectively utilize the information as supplied from either one of them.

The system uses schematic position (X1, Y1) in the observation direction to display an estimated content at a time T at which the user has reached a location in front of the system. Here, items (A to E) are displayed including the destination, the fee charged and so forth.

And, within the "system operable range," select the display content with increased accuracy by use of the gaze-point detection of the gaze detection apparatus 50.

Sixth Embodiment

A sixth embodiment will be described below. FIG. 40 is a block diagram of a ticket selling machine 200 in accordance with this embodiment.

This ticket machine 200 is constituted from a control section 202, a ticket dealing section 204, an image display section 206, an designated-position input section 208, and a speech recognition section 210.

An operation of the control section 202 will be first explained.

In the initial state where nobody is present, the control section 202 allows the gaze-point estimation section 130 to detect the user who is coming closer thereto from a distant position and then measure the direction of the user's gaze point and the system-to-user distance. Also, it calculates a partial region in the entire surface of the railroad network map presented at the upper portion of the ticket machine 200, which region matches the gaze-point direction at this time.

When it is detected that a measurement result of the distance between the gaze-point estimation section 130 and the user is equal to or less than a fixed threshold value, the control section 202 causes the partial region of the entire railroad network map designated by the gaze point that is measured by the gaze-point estimation section 130 to be displayed at the image display section 206 provided on the surface of the ticket machine 200.

Next, the gaze detection apparatus 50 is rendered operative measuring the direction of the user's gaze point. The ticket machine 200 has a touch panel for measurement of the coordinates of a point on the display screen of the image display section 206 when the user touched it by his or her finger, and an additional button(s) for manual operation. The machine 200 also has the designated position input section 208 for inputting either the designated position on the touch panel or an activation signal of the operation button. Machine 200 further has the speech recognition section 210 which recognizes the user's speech.

The control section 202 transmits a trigger signal to the gaze detection apparatus 50 when the user attempts to operate either the touch panel or the button, or when s/he generates voice; here, the gaze-point direction is measured instantly upon input of such trigger signal.

In the case where the user's operation is the operation with respect to the touch panel and where the distance between the coordinates of the user's finger touch point as inputted from the instruction position input section 208 and either one of a station title and a symbol indicating the station on the railroad network map being displayed on the display screen is equal to or less than a predetermined threshold value, one specific station title or its symbol which is the nearest to such designated coordinate point is displayed with adequate visual emphasis; then, the display-emphasized station title is sent to the ticket dealing section 204 for sale of a corresponding ticket.

Where the user's operation is voice generation, and when there is found a station title having voice similarity greater than a predefined threshold value as a result of identification by the speech recognition section 210 of the user's voice with the dictionary which records therein several voice information as to the station titles available, the station title or its symbol is then displayed with visual emphasis on the image display section 206, while sending its corresponding station title to the ticket dealing section 204 for sale of a ticket.

The user's operation could be other than the foregoing operations; namely, the user can touch an invalid portion of the touch panel except the station-title display section, depress the operation button, or generate certain word or phrase unrecognizable for the system as the station title, such as saying "this." If this is one of these cases, a cross-point or intersection is calculated between the gaze-point direction calculated by the gaze detection apparatus 50 and the display plane of the image display section 206 in the ticket machine 200. Then, one station title or station symbol which is the nearest to the coordinates of resultant intersection is displayed with visual emphasis.

Under this condition, when the user depressed the operation button within a predetermined length of time period, a corresponding station title is sent to the ticket dealing section 204 for sale of a ticket concerned. If the user failed to depress the operation button during such fixed time period then the emphasis-display of the image display section 206 is canceled returning to the trigger-signal wait state.

The ticket dealing section 204 finds the passenger's transportation fee or train fare from an input station to a target station; after counting the amount of user's charged money, it performs issuance of a ticket(s) and payment of the change, if any.

We claim:

1. A gaze detection apparatus for detecting a gaze point of a user who makes use of a system or apparatus operable by human's manual operation, characterized by comprising:

an image input means for sensing an image of said user;

eye detection means for detecting eyes of said user from said image as sensed by said image input means;

pupil detection means for obtaining positions of pupils in said eyes detected by said eye detection means;

three or more light emission means for emitting light toward said user;

reference point detection means for detecting respective reflecting positions of illumination light of said three or more light emission means on the eyes of said user; and gaze point detection means for detecting the gaze point of said user based on the three or more reflecting positions detected by said reference point detection means and the positions of said pupils as detected by said pupil detection means.

2. The gaze detection apparatus according to claim 1, characterized in that said eye detection means compares said image sensed by said image input means with the three or more reflecting positions detected by said reference point detection means thereby determining as eyes the nearby region of said reflecting positions in said image.

3. The gaze detection apparatus according to claim 1, characterized in that said gaze point detection means detects three or more reflecting positions to be detected by said reference point detection means and said pupil positions to be detected by said pupil detection means with the light emission position of each said three or more light emission means being as a reference.

4. A gaze detection method for detecting a gaze point of a user who makes use of a system or apparatus operable by human's manual operation, characterized by comprising:

an image input step for sensing an image of said user;

an eye detection step for detecting eyes of said user from said image as sensed by said image input means;

a pupil detection step for obtaining positions of pupils in said eyes detected at said eye detection step;

a reference point detection step for detecting on the eyes of said user respective reflecting positions of illumination light of three or more light emission means for emitting light toward said user; and a gaze point detection step for detecting a gaze point of said user based on the three or more reflecting positions detected at said reference point detection step and the positions of said pupils detected at said pupil detection step.

5. The gaze detection method according to claim 4, characterized in that said eye detection step compares said image sensed at said image input step with the three or more reflecting positions detected at said reference point detection step thereby determining as eyes the nearby region of said reflecting positions in said image.

6. The gaze detection method according to claim 4, characterized in that said gaze point detection step detects three or more reflecting positions to be detected at said reference point detection step and said pupil positions to be detected at said pupil detection step with the light emission position of each said three or more light emission means being as a reference.

7. A gaze detection apparatus for detecting a gaze point of a user who makes use of a system or apparatus operable by human's manual operation, characterized by comprising:

image input means for inputting an image of said user;

face image extraction means for extracting a face image of said user from said image as input by said image input means;

eye's inner corner detection means for detecting a position of an inner corner of at least one eye from said face image extracted by said face extraction means;

pupil detection means for detecting a position of a pupil in said eye from the face image extracted by said face extraction means; and gaze point detection means for obtaining a vector extending from the position of said inner corner of the eye detected by said eye's inner corner detection means to the position of said pupil detected by said pupil detection means, and for making use of resultant vector to detect the gaze point of said user.

8. A gaze detection apparatus for detecting a gaze point of a user who makes use of a system or apparatus operable by human's manual operation, characterized by comprising:

image input means for inputting an image of said user;

face image extraction means for extracting a face image of said user from said image as input by said image input means;

eye detection means for detecting a position of an inner or outer corner of at least one eye from said face image extracted by said face extraction means;

mouth/nose detection means for detecting a position of a mouth or a nostril from the face image extracted by said face extraction means;

face direction calculation means for calculating a face direction plane connecting between inner corner positions or outer corner positions of both eyes detected by said eye detection means and the position of the mouth or nostril detected by said mouth/nose detection means; and gaze point detection means for detecting a gaze point of said user based on a perpendicular vector of said face direction plane calculated by said face direction plane calculation means.

9. An information display apparatus for displaying information, characterized by comprising:

gaze point detection means for detecting a gaze point of a user of said information display apparatus;

prediction means for predicting information as required by said user based on said gaze point detected by said gaze point detection means; and information display means for performing displaying of the information predicted by said prediction means.

10. The information display apparatus according to claim 9, characterized in that said prediction means comprises:

prediction change means for, upon movement of said gaze point detected by said gaze point detection means, repredicting information as necessary for said user based on said gaze point moved; and display change means for instructing said information display means so as to display the information repredicted by said prediction change means.

11. The information display apparatus according to claim 9, characterized in that where said gaze point detected by said gaze point detection means is within said information display means, said prediction means predicts information necessary for said user based on such steadily looked information, and that where said gaze point detected by said gaze point detection means is out of said information display means, said prediction means predicts information necessary for said user based on that steadily looked portion.

12. A gaze detection method for detecting a gaze point of a user who makes use of a system or apparatus operable by human's manual operation, characterized by comprising:

an image input step for inputting an image of said user;

a face image extraction step for extracting a face image of said user from said image as input at said image input step;

an eye's inner corner detection step for detecting a position of an inner corner of at least one eye from said face image extracted at said face extraction step;

a pupil detection step for detecting a position of a pupil in said eye from the face image extracted at said face extraction step; and a gaze point detection step for obtaining a vector extending from the position of said inner corner of the eye detected at said eye's inner corner detection step to the position of said pupil detected at said pupil detection step, and for using resultant vector to detect the gaze point of said user.

13. A gaze detection method for detecting a gaze point of a user who makes use of a system or apparatus operable by human's manual operation, characterized by comprising:

an image input step for inputting an image of said user;

a face image extraction step for extracting a face image of said user from said image as input at said image input step;

an eye detection step for detecting a position of an inner or outer corner of at least one eye from said face image extracted at said face extraction step;

a mouth/nose detection step for detecting a position of a mouth or a nostril from the face image extracted at said face extraction step;

a face direction calculation step for calculating a face direction plane connecting between inner corner positions or outer corner positions of both eyes detected at said eye detection step and the position of the mouth or nostrils detected at said mouth/nose detection step; and a gaze point detection step for detecting a gaze point of said user based on a perpendicular vector of said face direction plane calculated at said face direction plane calculation step.

14. An information display method for displaying information, characterized by comprising:

a gaze point detection step for detecting a gaze point of a user of said information display apparatus;

a prediction step for predicting information as required by said user based on said gaze point detected at said gaze point detection step; and an information display step for performing displaying of the information predicted at said prediction step.

15. The information display method according to claim 14, characterized in that said prediction step comprises:

a prediction change step for, upon movement of said gaze point detected at said gaze point detection step, repredicting information necessary for said user based on said gaze point moved; and a display change step for instructing said information display means so as to display the information repredicted at said prediction change step.

16. The information display method according to claim 14, characterized in that where said gaze point detected at said gaze point detection step is within said information display means, said prediction step predicts information necessary for said user based on the steadily looked information thereof, and that where said gaze point detected at said gaze point detection step is out of said information display means, said prediction step predicts information necessary for said user based on that steadily looked portion.

17. An information display apparatus for displaying information, characterized by comprising:

distance measurement means for obtaining a distance between said information display apparatus and a user thereof;

gaze point detection means for detecting a gaze point of said user by selecting a detection method of gaze point in accordance with the distance measured by said distance measurement means;

prediction means for predicting information as required by said user based on said gaze point detected by said gaze point detection means; and information display means for performing displaying of the information predicted by said prediction means.

18. An information display method for displaying information by use of information display means, said method comprising:

a distance measurement step for obtaining a distance between said information display means and a user thereof;

a gaze point detection step for detecting a gaze point of said user by selecting a detection method of gaze point in accordance with the distance measured at said distance measurement step;

a prediction step for predicting information as required by said user based on said gaze point detected at said gaze point detection step; and an information display step for performing displaying of the information as predicted at said prediction step.

* * * * *